US008460597B2

(12) United States Patent
Mullane et al.

(10) Patent No.: US 8,460,597 B2
(45) Date of Patent: *Jun. 11, 2013

(54) METHOD OF PRODUCING COLOR CHANGE IN A SUBSTRATE

(75) Inventors: Timothy Ian Mullane, Union, KY (US); Kelyn Anne Arora, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 343 days.

This patent is subject to a terminal disclaimer.

(21) Appl. No.: 13/053,894

(22) Filed: Mar. 22, 2011

(65) Prior Publication Data

US 2012/0242009 A1    Sep. 27, 2012

(51) Int. Cl.
*B29C 59/16* (2006.01)

(52) U.S. Cl.
USPC .......................... 264/448; 264/245; 264/345

(58) Field of Classification Search
USPC ......................... 264/448, 245, 345
See application file for complete search history.

(56) References Cited

U.S. PATENT DOCUMENTS

| | | |
|---|---|---|
| 3,414,459 A | 12/1968 | Wells |
| 3,547,723 A | 12/1970 | Gresham |
| 3,556,907 A | 1/1971 | Nystrand |
| 3,708,366 A | 1/1973 | Donnelly |
| 3,738,905 A | 6/1973 | Thomas |
| 3,867,225 A | 2/1975 | Nystrand |
| 4,438,167 A | 3/1984 | Schwarz |
| 4,483,728 A | 11/1984 | Bauernfeind |
| 4,705,742 A | 11/1987 | Lewis |
| 4,826,550 A | 5/1989 | Shimizu et al. |
| 4,834,741 A | 5/1989 | Sabee |
| 4,968,313 A | 11/1990 | Sabee |
| 5,143,679 A | 9/1992 | Weber |
| 5,156,793 A | 10/1992 | Buell et al. |
| 5,167,897 A | 12/1992 | Weber et al. |
| 5,197,958 A | 3/1993 | Howell |
| 5,202,173 A | 4/1993 | Wu et al. |
| 5,246,433 A | 9/1993 | Hasse |
| 5,254,111 A | 10/1993 | Cancio et al. |
| 5,296,184 A | 3/1994 | Wu et al. |

(Continued)

FOREIGN PATENT DOCUMENTS

| | | |
|---|---|---|
| EP | 0934737 A1 | 8/1999 |
| JP | 2001123088 | 5/2001 |

(Continued)

OTHER PUBLICATIONS

U.S. Appl. No. 12/766,730, filed Apr. 23, 2010, Kelyn Anne Arora et al.

(Continued)

*Primary Examiner* — James Sanders
(74) *Attorney, Agent, or Firm* — Melody A. Jones; Jay A. Kreps

(57) ABSTRACT

The present invention relates to a method of producing color change in a substrate. The substrate includes an activatable colorant and a region that is heated prior to activating the activatable colorant. The substrate is exposed to electromagnetic radiation producing a first activated color region in the heated region and a second activated color region in a non heated region. The first activated color region appears in a different shade than the second activated color region.

18 Claims, 8 Drawing Sheets

U.S. PATENT DOCUMENTS

| | | | |
|---|---|---|---|
| 5,338,504 A | 8/1994 | Wang et al. |
| 5,354,597 A | 10/1994 | Capik et al. |
| 5,464,401 A | 11/1995 | Hasse et al. |
| 5,468,323 A | 11/1995 | McNeil |
| 5,503,076 A | 4/1996 | Yeo |
| 5,518,801 A | 5/1996 | Chappell et al. |
| 5,527,304 A | 6/1996 | Buell |
| 5,575,783 A | 11/1996 | Clear |
| 5,591,155 A | 1/1997 | Nishikawa |
| 5,628,097 A | 5/1997 | Benson et al. |
| 5,628,741 A | 5/1997 | Buell |
| 5,650,214 A | 7/1997 | Anderson et al. |
| 5,658,639 A | 8/1997 | Curro et al. |
| 5,674,216 A | 10/1997 | Buell |
| 5,691,035 A | 11/1997 | Chappell |
| 5,710,094 A | 1/1998 | Minami et al. |
| 5,723,087 A | 3/1998 | Chappell |
| 5,730,961 A | 3/1998 | Goudjil |
| 5,779,691 A | 7/1998 | Schmitt |
| 5,891,544 A | 4/1999 | Chappell |
| 5,916,661 A | 6/1999 | Benson et al. |
| 5,916,663 A | 6/1999 | Chappell |
| 5,968,025 A | 10/1999 | Roe et al. |
| 6,027,483 A | 2/2000 | Chappell |
| 6,080,415 A | 6/2000 | Simon |
| 6,086,715 A | 7/2000 | McNeil |
| 6,092,002 A | 7/2000 | Kastman et al. |
| 6,258,308 B1 | 7/2001 | Brady et al. |
| 6,277,466 B1 | 8/2001 | McNeil et al. |
| 6,306,409 B1 | 10/2001 | Ogawa et al. |
| 6,330,730 B1 | 12/2001 | Davies et al. |
| 6,368,444 B1 | 4/2002 | Jameson et al. |
| 6,383,431 B1 | 5/2002 | Dobrin et al. |
| 6,395,133 B1 | 5/2002 | McNeil |
| 6,476,289 B1 | 11/2002 | Buell et al. |
| 6,596,669 B1 | 7/2003 | Maruyama et al. |
| 6,710,221 B1 | 3/2004 | Pierce et al. |
| 6,719,742 B1 | 4/2004 | McCormack et al. |
| 6,794,023 B1 | 9/2004 | Melik et al. |
| 6,811,643 B2 | 11/2004 | McAmish |
| 6,818,295 B2 | 11/2004 | Bond et al. |
| 6,821,612 B1 | 11/2004 | Melik et al. |
| 6,843,949 B2 | 1/2005 | Brady et al. |
| 6,846,172 B2 | 1/2005 | Vaughn et al. |
| 6,849,319 B2 | 2/2005 | Cree et al. |
| 6,911,022 B2 | 6/2005 | Steger et al. |
| 6,946,506 B2 | 9/2005 | Bond et al. |
| 6,984,770 B2 | 1/2006 | Graeme, III et al. |
| 7,183,231 B2 | 2/2007 | Hoying et al. |
| 7,270,861 B2 | 9/2007 | Broering et al. |
| 7,306,582 B2 | 12/2007 | Adams et al. |
| 7,311,696 B2 | 12/2007 | Christon et al. |
| 7,402,157 B2 | 7/2008 | Christon et al. |
| 7,485,403 B2 | 2/2009 | Khan |
| 2003/0087566 A1* | 5/2003 | Carlyle et al. ................ 442/59 |
| 2003/0091803 A1 | 5/2003 | Bond et al. |
| 2003/0109605 A1 | 6/2003 | Bond et al. |
| 2004/0170813 A1 | 9/2004 | Digiacomantonia et al. |
| 2004/0265534 A1 | 12/2004 | Curro et al. |
| 2005/0021753 A1 | 1/2005 | Coleman |
| 2005/0064136 A1 | 3/2005 | Turner et al. |
| 2005/0123726 A1 | 6/2005 | Broering et al. |
| 2005/0170726 A1 | 8/2005 | Brunson et al. |
| 2005/0256479 A1 | 11/2005 | Carlucci et al. |
| 2006/0021536 A1 | 2/2006 | Song et al. |
| 2006/0025735 A1 | 2/2006 | Berg, Jr. et al. |
| 2006/0025736 A1 | 2/2006 | Berg, Jr. et al. |
| 2006/0025737 A1 | 2/2006 | Song et al. |
| 2006/0068168 A1 | 3/2006 | Olson et al. |
| 2006/0072429 A1 | 4/2006 | Nagai et al. |
| 2006/0087053 A1 | 4/2006 | Odonnell et al. |
| 2006/0089071 A1 | 4/2006 | Leidig et al. |
| 2006/0246802 A1 | 11/2006 | Hughes et al. |
| 2006/0286343 A1 | 12/2006 | Curro |
| 2007/0154687 A1 | 7/2007 | Luthi et al. |
| 2007/0156106 A1 | 7/2007 | Klofta et al. |
| 2008/0091162 A1 | 4/2008 | Maldonado et al. |
| 2008/0132865 A1 | 6/2008 | Li et al. |
| 2008/0195072 A1 | 8/2008 | Warner |
| 2008/0206529 A1 | 8/2008 | Veminami et al. |
| 2008/0228157 A1 | 9/2008 | McKiernan et al. |
| 2008/0233379 A1 | 9/2008 | O'Connor |
| 2008/0234644 A1 | 9/2008 | Hansson et al. |
| 2008/0269704 A1 | 10/2008 | Hansson et al. |
| 2008/0277621 A1 | 11/2008 | MacDonald et al. |
| 2008/0279253 A1 | 11/2008 | MacDonald et al. |
| 2008/0287903 A1 | 11/2008 | Vega et al. |
| 2008/0305328 A1 | 12/2008 | Green et al. |
| 2009/0030390 A1 | 1/2009 | Hammons et al. |
| 2009/0058892 A1 | 3/2009 | VanDemark |
| 2009/0143516 A1 | 6/2009 | MacDonald et al. |
| 2009/0191476 A1 | 7/2009 | Rogers et al. |
| 2009/0191480 A1 | 7/2009 | Rogers et al. |
| 2010/0201024 A1* | 8/2010 | Gibson et al. ................ 264/156 |
| 2011/0106035 A1 | 5/2011 | Arora et al. |

FOREIGN PATENT DOCUMENTS

| | | |
|---|---|---|
| JP | 2002138322 | 5/2002 |
| JP | 2003/199791 A | 7/2003 |
| JP | 2007/050145 A | 3/2007 |
| WO | WO-2006/018640 | 2/2006 |
| WO | WO-2007/001270 A1 | 1/2007 |
| WO | WO-2007/032710 A1 | 3/2007 |
| WO | WO-2006/114600 A2 | 5/2007 |
| WO | WO-2009/093028 A2 | 7/2009 |
| WO | WO-2009/081385 A2 | 8/2009 |
| WO | WO-2009/112956 A2 | 9/2009 |
| WO | WO 2011/025486 A1 | 3/2011 |

OTHER PUBLICATIONS

U.S. Appl. No. 12/766,705, filed Apr. 23, 2010, Kelyn Anne Arora et al.

U.S. Appl. No. 12/766,716, filed Apr. 23, 2010, Kelyn Anne Arora et al.

U.S. Appl. No. 12/766,698, filed Apr. 23, 2010, Kelyn Anne Arora et al.

U.S. Appl. No. 12/611,965, filed Nov. 4, 2009, Kelyn Anne Arora et al.

* cited by examiner

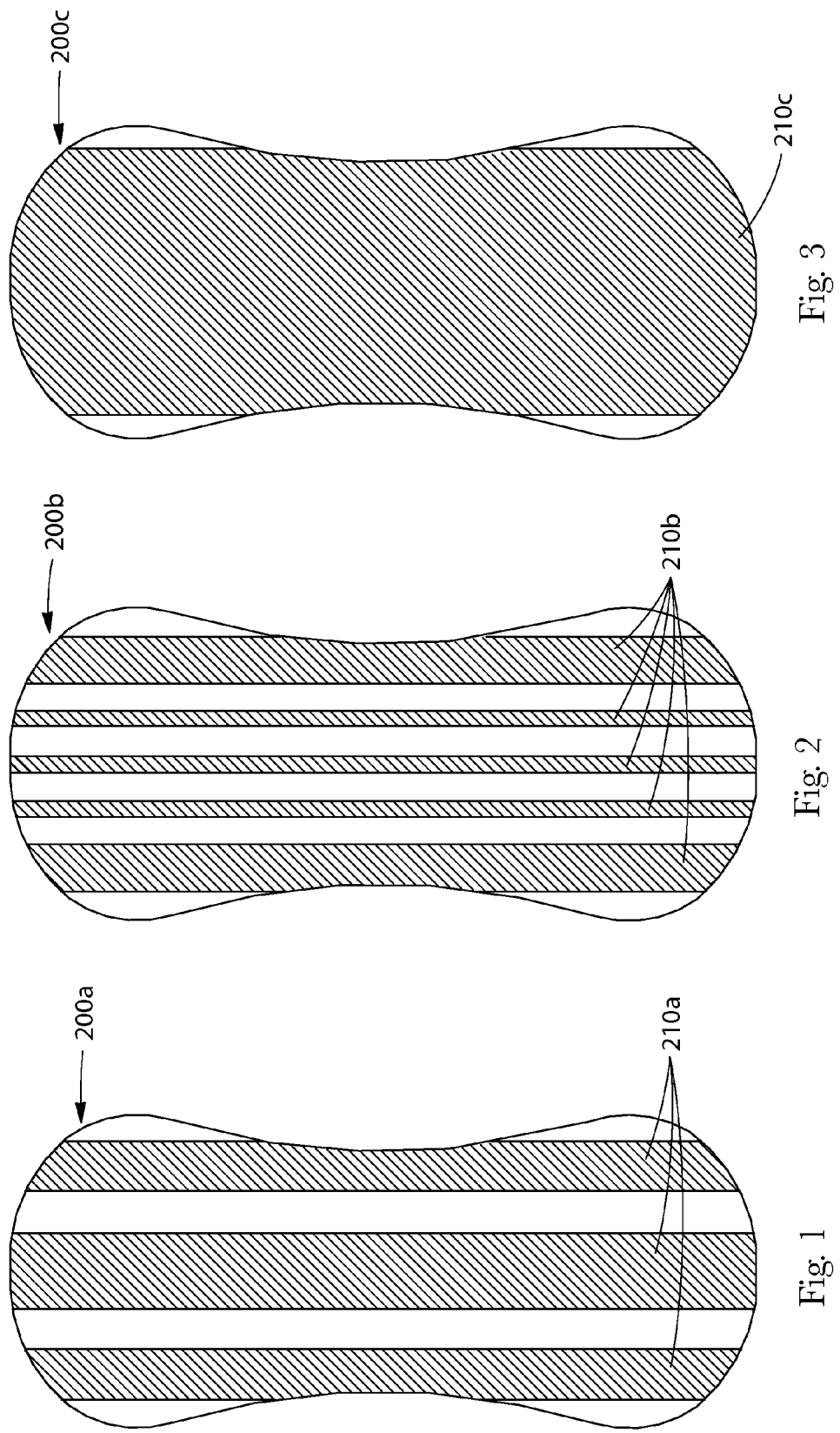

METHOD OF PRODUCING COLOR CHANGE IN A SUBSTRATE

FIELD OF THE INVENTION

The present invention is related to activatable colorants that are activated to produce color. Specifically, the invention is related to a method of producing color change in substrates comprising activatable colorants where the substrate includes regions that are heated prior to activating the activatable colorants such that the colors of the heated regions appear in a different contrast than the non heated regions.

BACKGROUND OF THE INVENTION

A variety of absorbent articles that include different colored regions are available in the market. For instance, absorbent articles such as sanitary napkins and female adult incontinence articles that function to collect fluid discharged from a woman's vagina or urethra sometimes include colored regions to highlight various sections of the absorbent article. For instance the topsheet of the absorbent article may include deformed regions such as apertures proximal the central portion of the absorbent article that are highlighted by color regions that differ in color or shade from portions of the absorbent article remote from the central portion of the absorbent article. Such color regions can be made to provide a perception of depth that corresponds to absorbency. The topsheet may also include other deformed regions such as three dimensional surface structures forming ribs and grooves or tufts in different regions to provide softness and comfort during use. Such three dimensional surfaces can be highlighted by color regions to capture the consumers attentions and enhance the perception of softness. Highlighting three-dimensional features with color can be particularly important and effective for thin, low basis weight substrates, where the presence of the feature may be less noticeable when it is the same color as the region surrounding it. Absorbent articles such as sanitary napkins and diapers have also been known to include decorative designs on other portions of the article such as the backsheet that are appealing to consumers. Such decorative designs can be associated with mechanically deformed regions of the article to highlight functional features such as softness or elasticity.

Similarly, the topsheet of the absorbent article may include topical additives such as lotions or hydrophilic coatings proximal the central portion of the absorbent article that are highlighted by color regions that differ in color from portions of the absorbent article remote from the central portion of the absorbent article. Such color regions can be made to highlight regions including the topical additives. For most applications, it is preferred that the topical additives such as lotions not include colorants that can transfer to a wearer's skin or clothing. As a result, the colored regions and topical additive regions are typically produced independent of one another requiring registration.

High speed manufacturing lines can include equipment and processing to produce deformed regions in web substrates and to apply topical additives such as lotions to web substrates during production of articles such as disposable absorbent articles. Such equipment can represent a significant capital cost to manufacturing. Adding printing capability to the manufacturing process in order to highlight the deformed regions or regions including topical additives represents an additional capital cost and complexity in order to register the printing with the deformed regions and/or regions including the topical additive. For manufacturers to effectively manage the cost, it is advantageous to use existing manufacturing lines to continue manufacturing absorbent articles. In some instances, the approach manufacturers have chosen to provide for colored regions might not be easily adapted in order to provide for colored regions that coincide with other regions due to the crowded nature of the manufacturing line. Thus, if a manufacturer desires to provide for visual elements on deformed regions or regions of the absorbent article including topical additives, the manufacturer might have to retool the manufacturing line to provide for additional printing and registration capabilities, thus incurring significant additional capital cost.

With these limitations in mind, there is a need for providing color change in the regions of a web substrate including deformed regions and/or topical additives that occurs simultaneously with creation of the deformed region or application of the topical additive, thus eliminating the need for registration. In addition there is a need for web substrates having regions including topical additives such as lotion with colored regions that coincide with the topical additives regions that can be manufactured cost effectively using existing manufacturing capability. Still further there is a need for providing absorbent articles with colored regions coinciding with deformed regions and colored regions coinciding with topical additive regions without requiring additional printing or registration capabilities for registering the colored regions with the deformed regions and the topical additive regions.

SUMMARY OF THE INVENTION

Methods of producing web substrates comprising activatable colorants where a region of the web substrate is heated prior to activating the activatable colorant such that exposing the web substrate to electromagnetic radiation produces a first activated color region in the heated region and a second activated color region in a region that is not heated prior to activating the activatable colorant. The first and second activated color regions can have the same or different color but the first activated color region has a different shade than the second activated color region. The web substrate can be heated prior to activating the activatable colorant via a heated nip or alternatively during formation of apertures in the web substrate where the heated regions circumscribe the apertures. Alternatively, the web substrate can be heated during the formation of bond sites where the heated regions coincide with the bond sites. Alternatively, the web substrate can be heated during application of a heated topical additive. The heated topical additives can include lotions, hot melt adhesives, coatings, odor control compositions and perfumes.

In one embodiment, the method of producing activated color regions in a web substrate comprising an activatable colorant comprises heating a region of the web substrate forming a heated region and applying electromagnetic radiation to the web substrate to activate the activatable colorant producing a first activated color region in the heated region and a second activated color region in a region that is separate from the heated region. The web substrate may be subsequently mechanically deformed producing a plurality of deformed regions within at least one of the first activated color region or the second activated color region or both the first and second activated color regions. A plurality of third activated color regions are produced during formation of the deformed regions. The plurality of third activated color regions coincide with the plurality of deformed regions.

BRIEF DESCRIPTION OF THE DRAWINGS

These and other features, aspects and advantages of the present invention will become better understood with regard to the following description, appended claims, and accompanying drawings where:

FIG. 1 is a top view of an absorbent article including a topical additive according to the present invention.

FIG. 2 is a top view of an absorbent article including a topical additive according to the present invention.

FIG. 3 is a top view of an absorbent article including a topical additive according to the present invention.

DETAILED DESCRIPTION OF THE INVENTION

Definitions

Figure 6:
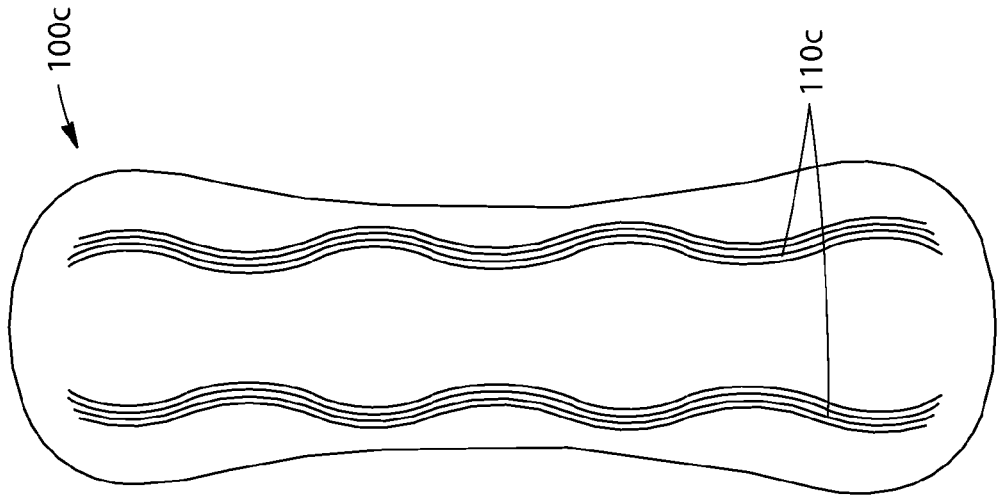
FIG. 6 is a top view of an absorbent article including a topical additive according to the present invention.

As used herein and in the claims, the term "comprising" is inclusive or open-ended and does not exclude additional unrecited elements, compositional components, or method steps.

As used herein, "machine direction" means the path that material, such as a web, follows through a manufacturing process.

As used herein "cross direction" means the path that is perpendicular to the machine direction in the plane of the web.

"Absorbent article" means devices that absorb and/or contain liquid. Wearable absorbent articles are absorbent articles placed against or in proximity to the body of the wearer to absorb and contain various exudates discharged from the body. Nonlimiting examples of wearable absorbent articles include diapers, pant-like or pull-on diapers, training pants, sanitary napkins, tampons, panty liners, incontinence devices, and the like. For the purpose of this invention, the term "absorbent article" not only includes the wearable portion of the article but also packaging for individual articles such as release paper wrappers (RPW) and applicators such as tampon applicators. Additional absorbent articles include wipes and cleaning products.

"Mechanical activation" is the mechanical deformation of one or more portions of an extensible material (e.g., film, nonwoven, fiber) that results in permanent elongation of the extensible material in the direction of activation in the X-Y plane of the material. Mechanical activation of a laminate that includes an elastic material joined to an extensible material typically results in one or more portions of the extensible material being at least partially permanently elongated, while the elastic material returns substantially to its original dimension.

"Mechanically activated" means a material that has been subjected to an activation process. Suitable examples of absorbent articles, absorbent article components and processes for activation can be found in U.S. Pat. Nos. 5,156,793; 4,438,167; 5,202,173; 5,254,111; 5,296,184; 5,354,597; 6,258,308; 6,368,444; 6,811,643; 6,821,612; 6,843,949; and 6,794,023.

"Direction of mechanical activation" means the direction in which the material is stretched in the X-Y plane during the mechanical activation process. For laminates comprising elastic materials laminated to extensible nonwovens or films, the direction of mechanical activation is also the direction in which the laminate is capable of stretching after completion of the activation process. For materials that do not exhibit elastic behavior, the direction of mechanical activation refers to the direction of the dimension in the X-Y plane of the material that is increased most as a result of the mechanical activation process. Examples of directions of mechanical activation include the machine direction, the cross direction, the longitudinal direction, the lateral direction, and diagonal direction.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaid, and bonded carded web processes, including carded thermal bonding. The basis weight of nonwoven fabrics is usually expressed in grams per square meter (g/m2). The basis weight of a laminate web is the combined basis weight of the constituent layers and any other added components. Fiber diameters are usually expressed in microns; fiber size can also be expressed in denier, which is a unit of weight per length of fiber. The basis weight of laminate webs suitable for use in the present invention can range from 6 g/m2 to 400 g/m2, depending on the ultimate use of the web. For use as a hand towel, for example, both a first web and a second web can be a nonwoven web having a basis weight of between 18 g/m2 and 500 g/m2.

As used herein, "spunbond fibers" refers to relatively small diameter fibers which are formed by extruding molten thermoplastic material as filaments from a plurality of fine, usually circular capillaries of a spinneret with the diameter of the extruded filaments then being rapidly reduced by an externally applied force. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky; to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer composition. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymer compositions extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross sectional area of the fiber and the various polymers are usually not continuous along the entire length of the fiber, instead usually forming fibers which start and end at random. Biconstituent fibers are sometimes also referred to as multi-constituent fibers.

As used herein, the term "non-round fibers" describes fibers having a non-round cross-section, and include "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

"Laminate" means two or more materials that are bonded to one another by methods known in the art, e.g. adhesive bonding, thermal bonding, ultrasonic bonding, extrusion lamination.

As used herein, the term "tampon" refers to any type of absorbent structure such as, e.g., an absorbent mass, that can be inserted into the vaginal canal or other body cavity, such as, e.g., for the absorption of fluid therefrom, to aid in wound healing, and/or for the delivery of materials, such as moisture or active materials such as medicaments. In general, the term "tampon" is used to refer to a finished tampon after the compression and/or shaping process.

As used herein, the term "pledget" refers to an absorbent material prior to the compression and/or shaping of the material into a tampon. Pledgets are sometimes referred to as tampon blanks or softwinds.

As used herein, the term "applicator" refers to a device or implement that facilitates the insertion of a feminine hygiene product, such as, e.g., a tampon or pessary, into an external orifice of a mammal Suitable applicators include, e.g., telescoping, tube and plunger, and compact applicators.

The term "color" as referred to herein includes any primary color, i.e., white, black, red, blue, violet, orange, yellow, green, and indigo as well as any declination thereof or mixture thereof. The term 'non-color' or 'non-colored' refers to the color white which is further defined as those colors having an L* value of at least 90, an a* value equal to 0±2, and a b* value equal to 0±2.

"Color change" herein means that at least a part of the substrate including an activatable colorant changes its color in response to an external stimulus. The change in color is visible from outside the substrate. A change in color "visible from outside the substrate" as used herein means that the color change is detectable by the naked human eye.

As used herein, "shade" particularly "a difference in shade" refers to a difference in the Chroma (or color saturation), calculated according to the formula:

$$\Delta C^* = [(a^*_{color2})^2 + (b^*_{color2})]^{1/2} - [(a^*_{color1})^2 + (b^*_{color1})^2]^{1/2}$$

where
a* and b* independently each represent a two color axis, a* representing the axis red/green (+a=red, −a=green), while b* represents the axis yellow/blue (+b=yellow, −b=blue).

"Activatable colorant" means a material which provides a color change in response to an external stimulus.

"External stimulus" means the exposure of the absorbent article to energy from outside the article in the form of pressure, temperature, electromagnetic radiation or combinations thereof.

"Activated color region" means areas containing a colorant that has been activated by external stimulus.

"Deformed region" means a region that has been strained sufficiently to produce distorted regions in the plane and/or out of the plane of the material.

"Visible" means those colors and wavelengths of light that are detectable by the human eye, nominally about 400-700 nanometers in wavelength.

"Electromagnetic radiation" means those areas of the spectrum amenable to industrial applications, such as the ultraviolet through the infrared wavelengths.

"Activatable chemistry" means those chemicals, monomers and polymers which are capable of being affected by an external stimulus.

"Disposable" means absorbent articles that are not intended to be laundered or otherwise restored or reused as absorbent articles (i.e., they are intended to be discarded after a single use and, preferably to be recycled, composted or otherwise disposed of in an environmentally compatible manner).

The present invention provides substrates containing activatable colorants that change color when exposed to external stimuli. The substrates can include webs such as wovens, nonwovens and films as well as extruded or molded articles such as containers, tampon applicators, etc. The activatable colorant can produce a color change that is reversible or irreversible. However, preferably the activatable colorant according to the present invention produces a color change that is irreversible, thereby providing a permanent visual effect. Sources of activatable colorants include 'thermochromic', which means that the color change is induced by a change of temperature, or 'photoreactive', which means that the color change is induced by electromagnetic radiation. Each of these sources of activatable colorants is discussed more fully below. An activatable colorant can also be 'piezochromic', where the color change is induced by pressure or pH sensitive such as a dye activated by change in pH.

Substrates can include a combination or blend of two or more activatable colorants where the activatable colorants are the same types but require different levels of external stimuli or different types requiring different types of external stimuli. For instance, for substrates including a blend of the same types of activatable colorants, the blend may include two different thermochromic colorants, whereas for substrates including a blend of different types of activatable colorants, the blend might include a thermochromic activatable colorant and a pH sensitive dye. Preferably the substrate according to the present invention includes a single activatable colorant that is both photoreactive and thermochromic.

The substrate according to the present invention can also include non activatable colorants. The non activatable colorant can include $TiO_2$ which is used to increase the opacity of the material. Non activatable colorant can also include a pigment. Pigments can be added to the substrate to provide an initial color which will affect the final color of activated color regions. For instance, a yellow pigment can be added to a substrate having an activatable colorant. If the activatable colorant ordinarily produces blue once activated, the yellow pigment will cause it to produce a green color once activated.

Once activated by an external stimulus, the activatable colorants form activated color regions in the substrate. The activated color regions can comprise uniform colored regions covering large sections or entire areas of the substrate or nonuniform colored regions comprising varying patterns of colored regions. Alternatively, the activated color regions can include multiple color patterns, zone patterns and multiple shades of a single color. The activatable colorants can also be activated to form activated color regions comprising written text, graphics, and intricate artwork.

The substrate according to the present invention preferably comprises an activatable colorant where the substrate is exposed to a first external stimulus comprising heat to form a heated region and a second external stimulus comprising electromagnetic radiation. The second external stimulus changes the heated region to a first color region and forms a second color region in an area of the substrate that is separate from the heated region (first color region). The first and second color regions can comprise different colors. Preferably the first and second color regions are the same color but the first color region is a darker shade than the second color region.

Using multiple shades (i.e., at least two) of a color and/or multiple shades and multiple colors together to create a perception of depth can engender in a user the perceived belief of better protection and enhanced functionality. For instance, color patterns forming concentric or congruent shapes comprising different shades of the same color where the lighter shade surrounds the darker shade or vice versa can be used to create a perception of depth which typically is not found with patterns comprised of different colors. Methods of measuring and quantifying the difference in color between a first shade and a second shade is disclosed in U.S. Pat. No. 7,402,157 B2 which is incorporated herein by reference.

The difference in color (i.e., $\Delta E^*$) between the first shade and the second shade should be at least 3.5. The $\Delta E^*$ is calculated by the formula $\Delta E^* = [(L^*_X - L^*_Y)^2 + (a^*_X - a^*_Y)^2 + (b^*_X - b^*_Y)^2]^{1/2}$. X may represent points 1, 2 or 3. Y may represent points 1, 2 or 3. X and Y should never be the same two points of measurement at the same time. In other words, $X \neq Y$. The difference in color between the second shade and the non-colored portion is at least 3.5. Preferably, the size of the colored portion ranges from about 5% to about 100% of the viewing surface of the topsheet. Also preferably, the first shade of the colored portion is positioned substantially centrally in relation to the second shade of the colored portion. However, so long as the shades are in proper spatial relationship to one-another such that the depth perception phenomena is created, any suitable positioning of the shades is suitable and foreseeable by one of skill in the art and are therefore acknowledged as suitable alternative embodiments of the invention.

The heated region is produced in the substrate by heating the region of the substrate to an elevated temperature that is close to the melting temperature of the activatable colorant. Preferably, the heated region is heated equal to or greater than the melting point temperature of the activatable colorant but below the melting point of the substrate. For example, the heated region may be heated to a temperature between 60 and 150° C., or preferably between 60 and 120° C. or more preferably between 60 and 100° C. Such heated regions can be produced in a web substrate by passing the substrate through rolls forming a heated nip and including a specific pattern which produces a patterned heated region on the web substrate. Heated regions can also be induced by strain using the methods fully described below. Alternatively, the heated regions can be formed in the web substrate during the formation of thermal bond sites, or apertures formed by applying heat or by applying heated topical additives forming topical additive regions. Such heated topical additives can include hot melt adhesives, lotions, odor control materials or coatings such as a fabric conditioning compositions. For the thermal bond sites and the topical additive regions, the heated regions coincide with the bond sites and the topical additive regions. For the apertures, the thermal regions circumscribe the apertures.

The heated region may be created immediately prior to the application of electromagnetic radiation and the substrate may or may not be at an elevated temperature when exposed to the electromagnetic radiation. Alternatively, the heating step may be performed in a separate or off-line step. The duration and/or temperature may be uniform within the heated region, or alternatively may vary by position on the substrate in order to create additional control over the shade in different areas or to create visual effects such as color gradients.

Without being bound by theory, it is believed that heating the activatable colorant above its melting point renders it more readily activatable by electromagnetic radiation or causes a greater portion of the colorant to become activatable.

For example, diacetylene compounds that are "activatable" may have a first solid form that is relatively non reactive to light, but upon heating are transformed into a second form that is relatively reactive to light and is thus capable of undergoing a color change. Without being limited by theory, this transformation could be a re-crystallization, crystal form modification, co-crystal combination or a melting/re-solidification process as disclosed in WO 2010/029329A1.

As mentioned above the web substrate according to the present invention preferably comprises an activatable colorant that has both photoreactive and thermochromic properties. Once the heated regions are formed in the substrate, the activatable colorant is activated by the second external stimulus comprising electromagnetic radiation which changes the heated regions to first color regions and produces second color regions coinciding with the unheated regions that are separate from the first color regions. The substrate can be subsequently exposed to a third external stimulus comprising heat to produce a third activated color region within the first, second or both the first and second activated color regions. Similar to the methods used in forming the heated regions previously described, the heat forming the third activated color region can be induced by strain or by other methods previously described used in forming the heated regions (such as thermal bond sites, heated topical additives, etc). Processes used in forming activated color regions in regions where the activatable colorant has been previously activated are disclosed in copending application Ser. Nos. 12/766,730 and 12/766,716 filed Apr. 23, 2010.

In a preferred embodiment, the third activated color regions are limited to areas within the first or second activated color regions. In other words, areas outside of the first or the second activated color regions that are exposed to the third external stimulus do not change color. For instance, in one embodiment, the second external stimulus comprising ultraviolet light can be exposed to the substrate in a particular pattern such that the first and second activated color regions are limited to certain portions of the substrate. Only those portions forming the first and second activated color region that are exposed to the third external stimulus comprising heat will change color forming third activated color regions. Portions of the substrate exposed to heat that are outside of the first and second activated color regions do not change color and therefore, do not form the third activated color region.

As mentioned above, the first external stimulus or the third external stimulus can comprise heat induced by application of a topical additive such as a hot melt adhesive, lotion, odor control material or coating such as a fabric conditioning composition. When applied as a first stimulus, the topical additive forms a topical additive region and a corresponding heated region in the web substrate prior to application of the second external stimulus comprising electromagnetic radiation and when applied to the substrate as a third external stimulus, subsequent to the second external stimulus comprising electromagnetic radiation, it changes the color of the substrate forming a third activated color region. When acting as the first stimulus, the topical additive region coincides with the heated region and when acting as the third stimulus, the topical additive region forms a third activated color region coinciding with the topical additive region. In either case, since the color change occurs as a result of the presence of the activatable colorant in the web substrate, the topical additive does not require a colorant. The topical additive is preferably translucent so that the second activated color region is visible through it and also so that the topical additive is not visible on a wearer's skin or stain a wearer's clothing once it transfers.

Alternatively, in some applications the topical additive can be opaque so that the second activated color region is initially hidden by the topical additive and eventually appears once a topical additive such as a lotion is used up.

The topical additive according to the present invention can include an adhesive such as a hot melt adhesive. Once the hot melt adhesive is added to a web substrate, a topical additive region comprising the hot melt adhesive is formed. The heat from the hot melt adhesive can form the heated region according to the present invention when applied as the previously described first stimulant or can activate the colorant in the substrate producing the third activated color region when applied as the previously described third stimulant. In the former case, the topical additive region forms the heated region which eventually forms the first activated color region once exposed to the second external stimulant comprising electromagnetic radiation. For the latter case, the topical additive region comprising the hot melt adhesive preferably overlaps the first or second activated color regions so that a third activated color region is produced within the first or second activated color regions. Whether applied as the first or third external stimulant, the resulting color regions can identify the location of the hot melt adhesive. In fact for applications requiring specific designs, the hot melt adhesive can be applied in patterns and the resulting color regions will coincide with the patterns.

Hot-melt adhesives used as construction adhesives in the manufacture of disposable absorbent articles typically include several components. These components include one or more polymers to provide cohesive strength, such as ethylene-vinyl acetate, copolymers, polypropylene, phenoxy resins, styrene-butadiene copolymers, ethylene-ethyl acrylate copolymers, low density polypropylenes, polyesters, polyamides, and polyurethanes. These polymers make up a significant part of the hot-melt adhesive composition. The composition also includes components such as, for example, a resin or analogous material (sometimes called a tackifier) to provide adhesive strength. Examples of such materials include hydrocarbons distilled from petroleum distillates, rosins and/or rosin esters, and terpenes derived, for example, from wood or citrus. The composition also typically includes waxes, plasticizers or other materials to modify viscosity. Examples of such materials include mineral oil, polybutene, paraffin oils, ester oils, and the like. Still further, the composition can optionally include additives, such as antioxidants or other stabilizers. A typical hot-melt adhesive composition might contain from about 15 to about 35 weight percent (wt. %) cohesive strength polymer(s); from about 50 to about 65 wt. % resin or other tackifier(s); from more than zero to about 30 wt. % plasticizer or other viscosity modifier; and optionally less than about 1 wt. % stabilizer or other additive.

FIGS. 1-3 illustrate examples of adhesive patterns used on a sanitary napkin absorbent article for personal hygiene. The embodiments shown include a panty liner 200a-c comprising adhesive patterns 210a-c used for securing the panty liner to the garments of a wearer. The adhesive patterns 210a-c can produce activated color regions coinciding with the adhesive patterns 210a-c.

In an alternate embodiment, the topical additive can include a lotion that is applied to a web substrate. Disposable absorbent articles, such as diapers, training pants, and catamenial devices having web substrates forming lotion topsheets are known. By applying a heated lotion to a topsheet including an activatable colorant according to the present invention, the region including the heated lotion can form an activated color region. When added to the substrate as a first external stimulant, prior to exposure to the second external stimulant (electromagnetic radiation), the heated lotion forms the heated region and first activated color region when exposed to electromagnetic radiation. Alternatively, when added to the substrate as a third external stimulus, subsequent to the second external stimulus (electromagnetic radiation), a third activated color region is formed coinciding with the topical additive region comprising lotion. The third activated color region coincides with the first or second activated color regions or both the first and second activated color regions.

Lotions of various types are known to provide various skin benefits, such as prevention or treatment of diaper rash as disclosed in U.S. Pat. No. 6,861,571 issued to Roe, et al, U.S. Pat. No. 5,607,760 issued to Roe and U.S. Pat. No. 5,643,588 issued to Roe, et al. Such lotion compositions comprise (1) an emollient(s); (2) an immobilizing agent(s); (3) optionally a hydrophilic surfactant(s); and (4) other optional components. These lotions can be applied to the topsheet of absorbent articles, for example, and can be transferred to the skin of the wearer during use. For instance, when applied to the outer surface of a diaper topsheets, the lotion compositions can be transferable to the wearer's skin by normal contact, wearer motion, and/or body heat. Since the activatable colorant is in the web substrate rather than the lotion, the second activated color region is produced in the web substrate and not in the lotion. Therefore, the color does not rub off onto the wearer or transfer to the wearer with the lotion.

In preparing lotioned absorbent articles according to the present invention, the lotion composition can be applied to the outer surface (i.e., body facing surface) of the topsheet, but can also be applied to the inner surface of the topsheet or to any other component of the absorbent article. Any of a variety of application methods that evenly distribute the lotion composition can be used. Suitable methods include spraying, printing (e.g., flexographic printing), coating (e.g., gravure coating), extrusion, or combinations of these application techniques, e.g. spraying the lotion composition on a rotating surface, such as a calender roll, that then transfers the composition to the outer surface of the topsheet. Lotion compositions of the present invention can be applied by printing methods, or continuous spray or extrusion as is known in the art, or as described in U.S. Pat. No. 5,968,025.

The lotion composition may be applied to the entire surface of the topsheet or portions thereof. The lotion composition can be applied in a stripe aligned with and centered on the longitudinal centerline of the disposable absorbent article. The lotion composition can be applied in a plurality of stripes having uniform or non-uniform widths. Alternatively the lotion can be aligned with and centered in opposition to the longitudinal centerline. It can be preferred that the lotion be applied in a plurality of stripes parallel to the longitudinal axis of the absorbent article. This allows for both transfer of the lotion to a broader area of the wearer.

Alternatively, the lotion composition can also be applied nonuniformly to the outer surface of the topsheet. By "non-uniformly" is meant that the amount, pattern of distribution, etc. of the lotion composition can vary over the topsheet surface. For example, some portions of the treated surface of the topsheet can have greater or lesser amounts of lotion composition, including portions of the surface that do not have any lotion composition on it. For example, the lotion composition can be applied on one region of the topsheet in the shape of a rectangle and/or a circle, and/or as multiplicity of dots.

Figure 5:
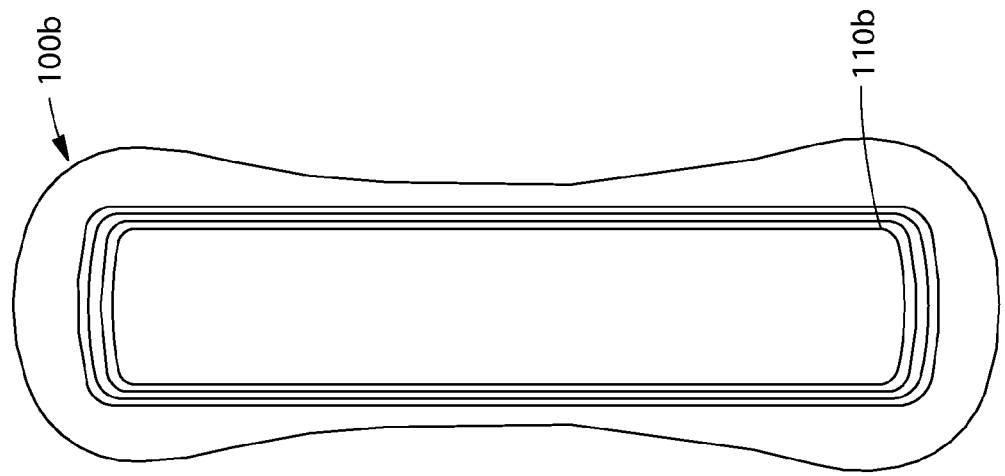
FIG. 5 is a top view of an absorbent article including a topical additive according to the present invention.
Figure 4:
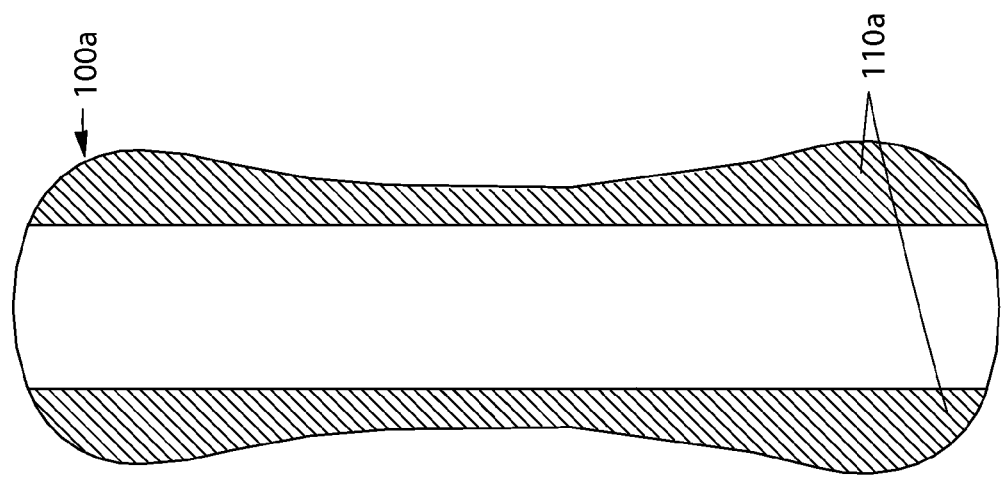
FIG. 4 is a top view of an absorbent article including a topical additive according to the present invention.

FIGS. 4 through 6 illustrate examples of lotion patterns used on a sanitary napkin absorbent article for personal hygiene. The embodiments shown include a panty liner 100a-c comprising lotion patterns 110a-c disposed on the skin facing surface of the panty liner 100a-c. The lotion patterns 110a-c can produce activated color regions coinciding with the lotion patterns 110a-c.

In an alternate embodiment, the topical additive can include a fabric conditioning composition that is applied to a web substrate. A fabric conditioning composition is typically used in dryer-activated fabrics as disclosed in U.S. Pat. No. 4,808,086 issued Feb. 28, 1989. Other applications for fabric conditioning compositions are disclosed in U.S. Pat. No. 5,094,761 and U.S. Pat. No. 5,929,026. For the present invention a web substrate comprising a dryer activated fabric can include an activatable colorant that is first activated by electromagnetic radiation such as UV light to produce a first activated color region. A fabric conditioning composition can be subsequently applied to the fabric producing topical additive regions within the first activated color region. The fabric conditioning composition is preferably applied at an elevated temperature sufficient to produce activated color regions within the topical additive regions identifying the presence of the fabric conditioning composition. Alternatively, the heated fabric conditioning composition can be applied to the fabric prior to exposure to electromagnetic radiation forming a heated region which subsequently forms a first color region when exposed to electromagnetic radiation.

In an alternate embodiment, the topical additive can include an odor control composition that is applied to a web substrate. Examples of odor control materials are described in WO 2010/148171A1 and WO 2008/018004A2.

As mentioned above, the first external stimulus and or the third external stimulus can also comprise heat induced by a heated nip such as thermal calendaring and thermal bonding and also mechanical deformation processes such as SELF, Micro SELF, rotary knife aperturing (RKA), hot pin, or embossing. Mechanical deformation processes are described more fully below. Processes resulting in generation of heat in the substrate such as dynamic mechanical bonding and ultrasonic bonding can also be used as first and third external stimuli. Dynamic mechanical bonding is disclosed in U.S. Pat. No. 4,854,984 and WO 2004/108037 A1.

The substrates according to the present invention can comprise web substrates such as films, nonwovens, air laids, laminates, fibers, filaments, particles and foams. Substrates according to the present invention can also include injection molded and blow molded articles. The activatable colorant can be blended into or coated onto material forming the substrate and can be disposed throughout or limited to only a portion of the substrate where a color pattern is desired. Alternatively, activatable colorants can be mixed or blended into a topical additive such as a lotion or adhesive and applied to a substrate.

The composition used to form the web substrates of the present invention, particularly films and nonwovens can include thermoplastic polymeric and non-thermoplastic polymeric materials. Non-thermoplastic materials include cellulosic materials such as rayon. For fibers and nonwovens, thermoplastic polymeric material used in forming fibers must have rheological characteristics suitable for melt spinning. The molecular weight of the polymer must be sufficient to enable entanglement between polymer molecules and yet low enough to be melt spinnable. For melt spinning, thermoplastic polymers have molecular weights below about 1,000,000 g/mol, preferably from about 5,000 g/mol to about 750,000 g/mol, more preferably from about 10,000 g/mol to about 500,000 g/mol and even more preferably from about 50,000 g/mol to about 400,000 g/mol. Unless specified elsewhere, the molecular weight indicated is the number average molecular weight.

The thermoplastic polymeric materials are able to solidify relatively rapidly, preferably under extensional flow, and form a thermally stable fiber structure, as typically encountered in known processes such as a spin draw process for staple fibers or a spunbond continuous fiber process. Preferred polymeric materials include, but are not limited to, polypropylene and polypropylene copolymers, polyethylene and polyethylene copolymers, polyester and polyester copolymers, polyamide, polyimide, polylactic acid, polyhydroxyalkanoate, polyvinyl alcohol, ethylene vinyl alcohol, polyacrylates, and copolymers thereof and mixtures thereof. Other suitable polymeric materials include thermoplastic starch compositions as described in detail in U.S. publications 2003/0109605A1 and 2003/0091803. Other suitable polymeric materials include ethylene acrylic acid, polyolefin carboxylic acid copolymers, and combinations thereof. Other suitable polymeric materials comprising starch and polymers are described in U.S. Pat. Nos. 6,746,766, 6,818,295, and 6,946,506. Common thermoplastic polymer fiber grade materials are preferred, most notably polyester based resins, polypropylene based resins, polylactic acid based resin, polyhydroxyalkanoate based resin, and polyethylene based resin and combination thereof. Most preferred are polyethylene and polypropylene based resins.

Activatable Colorant

As briefly described above, activatable colorants can be 'photoreactive', which means that the color change is induced by electromagnetic radiation, 'thermochromic', which means that the color change is induced by a change of temperature, or 'piezochromic', which means that the color change is induced by pressure. These definitions comprise materials changing color irreversibly, reversibly or quasi-reversibly in response to the respective stimulus. The activatable colorants herein can either be coated onto a web substrate, such as on film or nonwoven, or more preferably can form an integral part of the substrate by being added e.g. to the polymeric master batch these components are made of. The activatable colorants herein change their color in response to external stimuli as defined hereinbefore.

a) Photoreactive Materials

Photoreactive materials change color in response to exposure to electromagnetic radiation. The color change can be irreversible providing a permanent change in color or it can be reversible providing a temporary change in color.

Photochromic materials are those that reversibly change color when exposed to light or changes in light intensity. Photochromic materials typically provide a reversible color change transiting from a colorless state to a color state upon exposure to light and back to a colorless state when reversed. Examples for photochromic materials are described in U.S. Pat. No. 6,306,409; U.S. Pat. No. 6,080,415 or U.S. Pat. No. 5,730,961.

Polychromic materials are those which are capable of generating multiple colors. Compounds based upon diacetylene, X—C≡C—C≡C—Y, when polymerized, are known to take on different color properties. Polymerization is typically achieved by exposure to certain types of radiation, such as ultraviolet radiation. Varying the intensity of the radiation causes differing degrees of polymerization, and different colors.

It is known that these properties can be utilized to achieve multi-color printing. See, for example; U.S. Pat. No. 4,705,742, "Processless Multicolour Imaging", issued on Nov. 10, 1987, assigned to Gaf Corporation; and WO2006/018640, "Multi-colour printing", published on Feb. 23, 2006, Sherwood Technologies Ltd. Both of these documents disclose methods of applying coatings comprising various diacetylene compounds to the surface of a substrate for the purpose of irradiating and forming an image on the surface of the substrate. Particularly preferred materials are those that can be dispersed or blended into the polymeric matrix of the layers, such as those disclosed in PCT publication WO 2009/093028A2 and WO 2009/081385 A2, which are compounds which undergo a color change upon irradiation, and which have the general structure: X—C≡C—C≡C—Y—(CO)n-QZ wherein X is H, alkyl or —Y—(CO)n-QW; each Y is the same or a different divalent alkylene group; Q is O, S or NR; R is H or alkyl; W is H, alkyl or Z; each Z is the same or a different unsaturated alkyl group; and each n is 0 or 1.

Another example of a material of use in the present invention is a thermoplastic material comprising polymer mixed with a charge transfer agent and a photo acid generating agent such as those described in US 2009/0191476 A1. Exposure of the thermoplastic material comprising the charge transfer agent and photo acid generating agent to irradiation will bring about a color change reaction which can be used to create text, artwork, devices or other images and effects.

Web substrates according to the present invention preferably comprise photoreactive materials providing an irreversible, permanent change in color. Examples of photoreactive materials providing permanent color change are described in PCT publication WO 2009093028A2 which describes polychromic substances comprising diacetylene compounds that change color when subjected to irradiation. The type of radiation that performs the color change reaction with the diacetylene compounds includes laser or non-coherent, broadband or monochromatic radiation. Specific radiation types include ultraviolet, near, mid or far infrared, visible, microwave, gamma ray, x-ray or electron beam.

Ultraviolet irradiation is preferred for changing substrates comprising the diacetylene compounds from colorless or low visual color to color on exposure to ultraviolet irradiation, and then change to a color different to the first on subsequent exposure to infrared irradiation and/or heat. Heat can be applied directly, for example with heated tooling or the heat may be induced by strain during mechanical deformation of the web substrate. Methods for producing mechanical deformation are discussed more fully below. Methods of laser irradiation may be preferred for writing text and drawing intricate artwork directly on substrates comprising the diacetylene compounds, as laser imaging can be conveniently controlled by computer with the appropriate software and has superior resolution capability. However, similar effects can be obtained by passing radiation from, for example, an ultraviolet lamp through a mask before it reaches the substrates comprising the diacetylene compound.

Another application describing of photoreactive materials providing permanent color change includes WO 2009/081385 which describes thermoplastic material comprising polychromic substance wherein the polychromic substance is a functionalized diacetylene having a formula which has a general structure that is described therein.

Activation of photoreactive materials is preferably achieved using an ultraviolet lamp. One example is the Coil Clean (CC) Series ultraviolet fixtures available from American Ultraviolet (Lebanon, Ind.). Another UVC exposure unit suitable for use in activation of photoreactive materials consists of a metal enclosure containing 8 UV amalgam lamps and 8 ballasts with individual circuits for individual lamp controls and a fan for cooling lamps to maintain temperature. The lamps are 357 mm in length and are available from American Ultraviolet as part number GML750A.

Other examples of equipment that may be used for activation of photoreactive materials include the J3825 MonoCure Lamphead from Nordson UV Limited (Berkshire UK), the DropCure water cooled medium pressure mercury lamp from Nordson and the 270S UV Lamp Assembly and Power Supply by Integrated Technology. The type of lamp within the unit may be changed to vary the spectral output as needed. Examples of relevant bulb types include "H", "V", "D" and "Q".

b) Thermochromic Materials

Thermochromic pigments are organic compounds that effectuate a reversible or irreversible color change when a specific temperature threshold is crossed. A thermochromic pigment may comprise three main components: (i) an electron donating coloring organic compound, (ii) an electron accepting compound and (iii) a solvent reaction medium determining the temperature for the coloring reaction to occur. One example of a commercially available, reversible thermochromic pigment is 'ChromaZone® Thermobatch Concentrates available from Thermographic Measurements Co. Ltd. Thermochromic pigments and the mechanism bringing about the temperature triggered color change are well-known in the art and are for example described in U.S. Pat. No. 4,826,550 and U.S. Pat. No. 5,197,958. Other examples of thermochromic pigments are described in published US application 2008/0234644A1.

Thermochromic or temperature sensitive color changing fibers are known from the textile field to be used in clothing, sport equipment, etc. The fibers are either produced by blending a thermochromic pigment in the base resin from which the fibers are to be produced, for example a polyolefin, such as polyethylene or polypropylene, polyester, polyvinyl alcohol etc. or by using a thermochromic coloring liquid for the fibers. The production of temperature sensitive color-changing fibers are disclosed in for example JP2002138322 and JP2001123088. The fibers change color at a selected temperature. The change of color is either reversible or irreversible.

An example of a thermochromic fiber is one which is partly characterized in that the flexural modulus of elasticity of a base resin is within the range of 300-1,500 MPa in the temperature-sensing color-changing fiber. The fiber is formed by melt blending a thermally color-changing pigment in a dispersed state in the base resin of a polyolefin resin and/or the polyolefin resin blended with a thermoplastic resin. The fiber is further described in JP 2002-138322.

Alternatively, the thermosensitive pigment may be of a microcapsule type which is known in the art of thermosensitive pigments.

Activation of the activatable colorant in the web substrate according to the present invention can be carried out in a variety of different ways. As previously discussed, the external stimuli activating the activatable colorant in the web substrate according to the present invention includes a second external stimulus comprising electromagnetic radiation producing a first activated color region coinciding with the heated regions and a second activated color region that is separate from the first activated color region (heated region). The application of the second external stimulus (electromagnetic radiation) can be sequentially followed by a third external stimulus comprising heat. The preferred source of electromagnetic radiation is ultraviolet light and the source of heat can vary. For example, a web substrate can be unwound from a supply roll and exposed to a first external stimulus comprising heat forming a heated region and subsequently exposed to a second external stimulus comprising electromagnetic radiation such as ultraviolet light to induce color change and form a first and second activated color regions. A heated topical additive can be subsequently applied to the web substrate in regions within the first or second or both first and second activated color regions producing a third activated color region within the first or second or both first and second activated color regions.

In an alternate embodiment, a third external stimulus can be applied to the web substrate comprising heat induced by strain forming a third activated color region within the first or second or both first and second activated color regions. The strain is preferably caused by mechanical deformation during formation of a deformed region within the activated color region. Preferably, the third activated color region coincides with the deformed region.

The deformed regions can include apertures or bonded regions formed in the x-y plane of the web but preferably include elements protruding in a z direction out of the x-y plane of the web such as ridges and grooves, rib-like elements and tufts. Bonded regions can be produced via thermal bonding, calendaring, ultrasonic bonding and dynamic mechanical bonding. Apertures can be formed by a mechanical deformation processes such as rotary knife aperturing. Protruding elements can be formed via mechanical deformation processes including, but not limited to, ring rolling, SELF'ing, micro-SELF, and embossing. Mechanical deformation processes are discussed more fully below.

The heat induced by strain during formation of the deformed regions can result in third activated color regions exhibiting a color gradient which is proportional to the degree of deformation. The color gradient can be produced as a result of variable heat produced corresponding to variable strain during formation of the deformed regions. For instance, for three dimensional deformed regions comprising tufts formed via micro-SELF, the tufts can comprise a color gradient where the base and tip experience minimal color change since these regions experience little, if any, deformation and corresponding strain during formation of the tufts whereas the sides of the tuft experience heavy strain and corresponding heat resulting in major color change, Mechanical Deformation Processes Mechanical deformation processes use deformation members comprising counter rotating rolls, intermeshing belts or intermeshing two dimensional plates. The deformation members can be at ambient temperature or heated to an elevated temperature above ambient. When used in forming heated regions, the deformation members are preferably heated to at least the melting point temperature of the activatable colorant.

Figure 7:
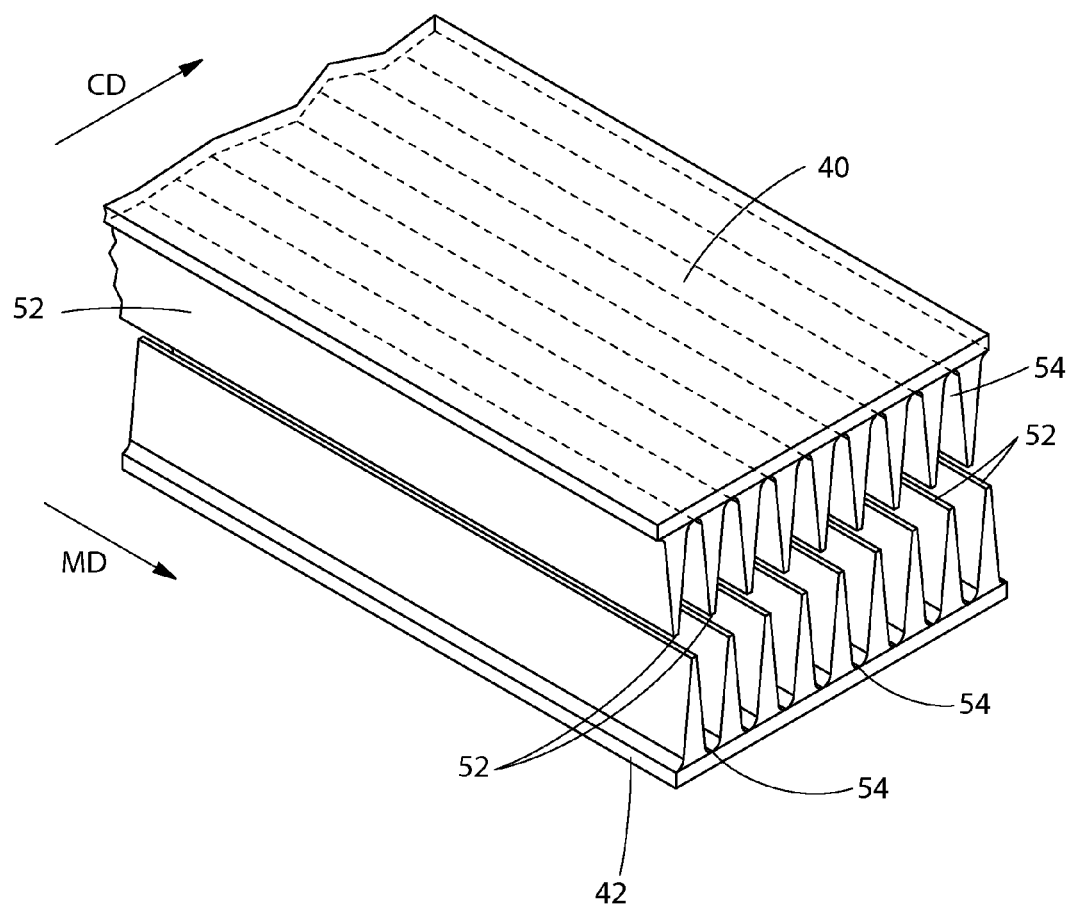
FIG. 7 is a perspective view showing portions of deformation members according to the present invention showing teeth and grooves arranged in a machine direction for incrementally stretching a web in the cross machine direction.
Figure 8:
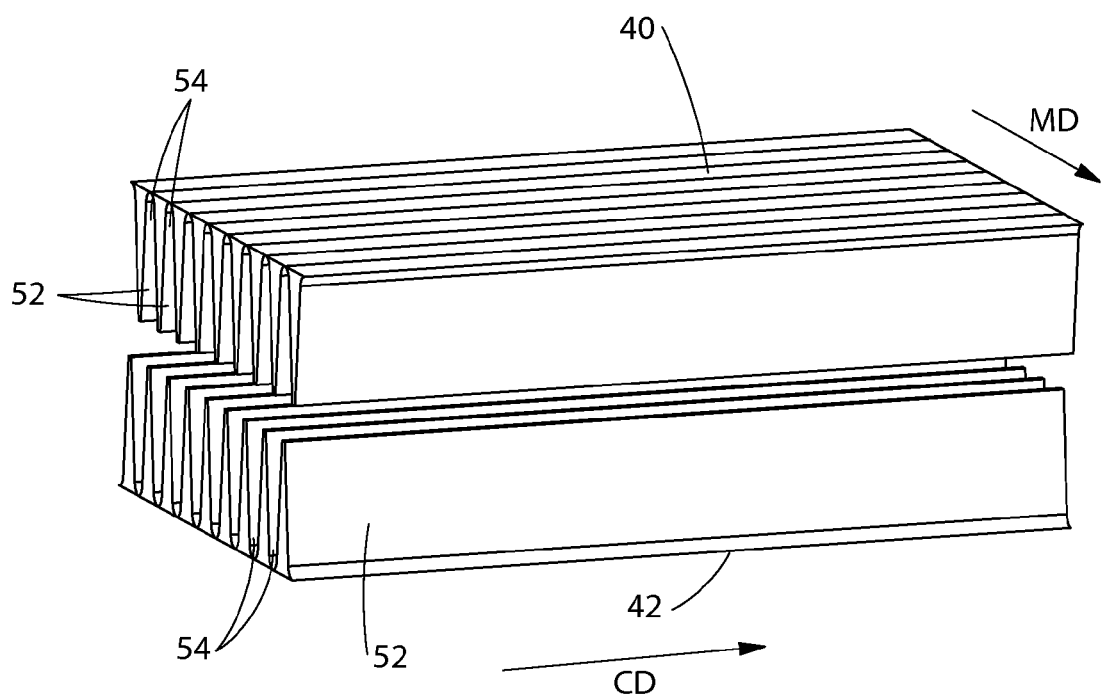
FIG. 8 is a perspective view showing portions of deformation members according to the present invention showing teeth and grooves arranged in a cross machine direction for incrementally stretching a web in the machine direction.

One mechanical deformation process which can be used to produce deformed regions and corresponding heat induced by strain in a web substrate is a process commonly referred to as ring rolling where intermeshing teeth and grooves of deformation members engage and stretch the web interposed therebetween. For ring rolling, the deformation members can be arranged to stretch the web in the cross machine direction or the machine direction depending on the orientation of the teeth and grooves. For instance, for incremental stretching in the cross machine direction CD as shown in FIG. 7, teeth 52 and grooves 54 on each deformation member 40, 42 are oriented in the machine direction MD. Conversely, for incremental stretching in the machine direction MD as shown in FIG. 8, the teeth 52 and grooves 54 on each deformation member 40, 42 are oriented in the cross machine direction CD. Deformation members comprising such cross machine direction teeth and grooves are kept in phase in the machine direction with respect to the intermeshing pattern.

Figure 9:
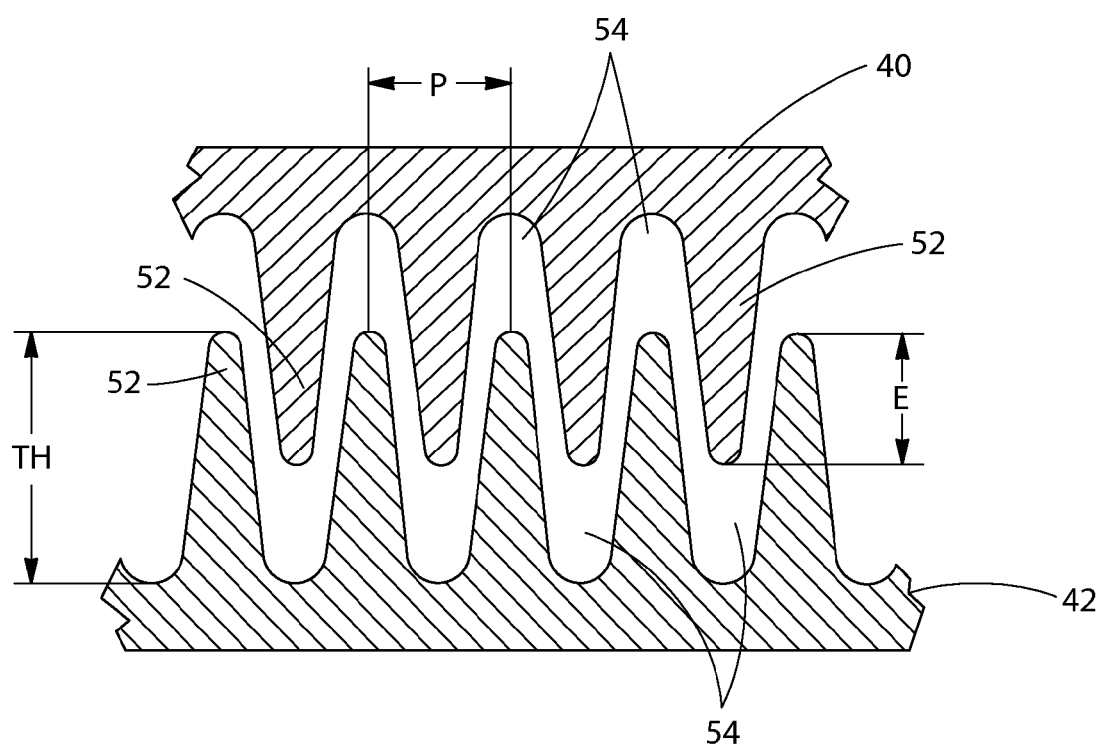
FIG. 9 is an enlarged, fragmentary, cross-sectional view showing the interengagement of teeth and grooves of deformation members as shown in FIG. 7 and FIG. 8.

FIG. 9 is an enlarged, fragmentary, cross-sectional view showing the interengagement of teeth 52 and grooves 54 of respective opposing deformation members 40, 42 in a deformation zone which stretch the web. Teeth 52 have a tooth height TH and are spaced apart from one another by a preferably uniform distance to define a tooth pitch P. As shown, teeth 52 of deformation member 40 extend partially into grooves 54 of the opposed deformation member 42 to define a "depth of engagement", E, as shown in FIG. 9. During deformation, the depth of engagement is controlled to gradually increase over at least a portion of the deformation zone.

Figure 10:
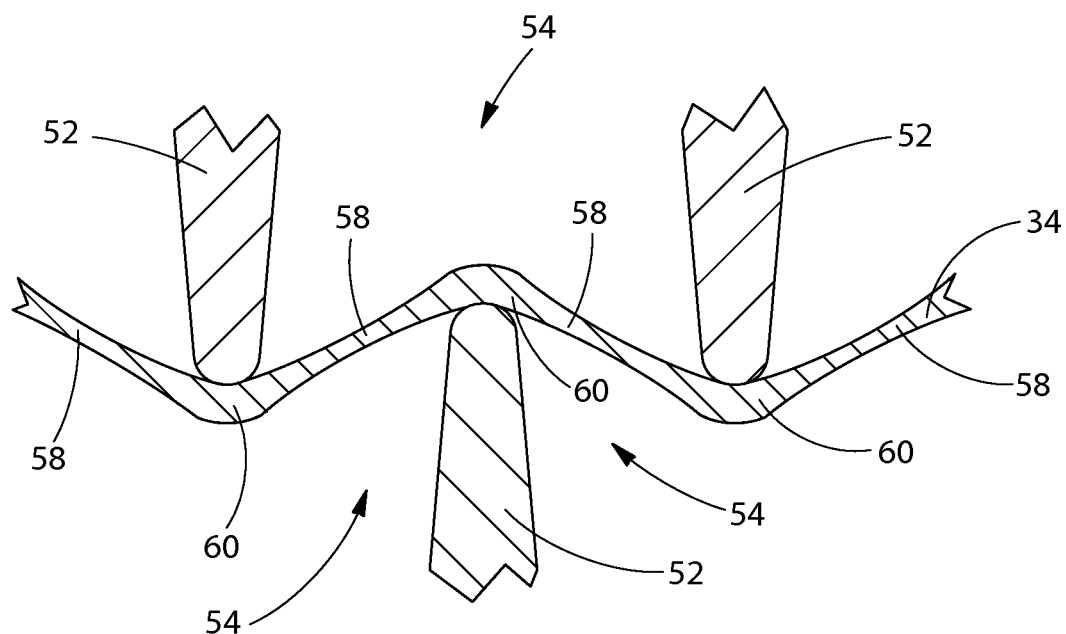
FIG. 10 is an even further enlarged view of the deformation members shown in FIG. 7 and FIG. 8 showing several interengaged teeth and grooves with a web of material therebetween.

FIG. 10 is an even further enlarged view of several interengaged teeth 52 and grooves 54 in the deformation zone with a web 34 of material therebetween. As shown, a portion of a web 34, which can be nonwoven web, is received between the interengaged teeth and grooves in the deformation zone. The interengagement of the teeth and grooves causes laterally spaced portions of web 34 to be pressed by teeth 52 into opposed grooves 54. In the course of passing between deformation members, the forces of teeth 52 pressing web 34 into opposed grooves 54 impose within web 34 tensile stresses that act in the machine or cross machine direction depending on the orientation of the teeth and grooves on the deformation members. The tensile stresses can cause intermediate web sections 58 that lie between and that span the spaces between the tips of adjacent teeth 52 to stretch or extend in a machine or cross machine direction, which can result in a localized reduction of the web thickness at each of intermediate web sections 58. For nonwoven webs, including air laid webs, the stretching can cause fiber reorientation, a reduction in basis weight, and controlled fiber destruction in the intermediate web sections 58.

Although the portions of web 34 that lie between the adjacent teeth are locally stretched, the portions of the web that are in contact with the tips of the teeth may not undergo a similar degree of extension. Because of the frictional forces that exist between the surfaces at the rounded outer ends of teeth 52 and the adjacent areas 60 of web 34 that are in contact with the tooth surfaces at the outer ends of the teeth, sliding movement of those portions of the web surfaces relative to the tooth surfaces at the outer ends of the teeth is minimized. Consequently, in some cases, the properties of the web 34 at those areas of the web that are in contact with the surfaces of the tooth tips change only slightly, as compared with the change in web properties that occur at intermediate web sections 58.

Teeth 52 can be generally triangular in cross section having generally rounded tooth tips, as shown in FIGS. 9 and 10. As shown teeth 52 have a tooth height TH (note that TH can also be applied to groove depth; in one embodiment tooth height and groove depth can be equal), and a tooth-to-tooth spacing referred to as the pitch P. The depth of engagement E, tooth height TH, and pitch P can be varied as desired depending on the properties of the webs being processed and the desired characteristics of the processed webs.

As will be appreciated by those skilled in the art, the sizes of the respective teeth and grooves can be varied within a wide range and would still be effective to carry out the present invention. In that regard, additional structural details of suitable deformation members according to the present invention are provided in U.S. Pat. No. 5,156,793, entitled "Method for Incrementally Stretching Zero Strain Stretch Laminate Sheet in a Non-Uniform Manner to Impart a Varying Degree of Elasticity Thereto," which issued on Oct. 20, 1992, to Kenneth B. Buell et al.; and in U.S. Pat. No. 5,167,897 entitled "Method for Incrementally Stretching a Zero Strain Stretch Laminate Sheet to Impart Elasticity Thereto," which issued on Dec. 1, 1992, to Gerald M. Weber et al. Other Activation patents include: U.S. Pat. No. 5,527,304, entitled "Absorbent Article with Elasticized Side Panels having Extension Panel," which issued on Jun. 18, 1996, to Buell; U.S. Pat. No. 5,674, 216, entitled "Absorbent Article with Elasticized Side Panels," which issued on Oct. 7, 1997, to Buell; U.S. Pat. No. 6,476,289, entitled "Garment having Elastomeric Laminate," which issued on Jun. 18, 1996, to Buell; U.S. Pat. No. 5,628, 741, entitled "Absorbent Article with Elastic Feature having a Prestrained Web Portion and Method for Forming Same," which issued on May 13, 1997, to Buell; U.S. Pat. No. 5,591, 155, entitled "Disposable Training Pant having Improved Stretchable Side Panels," which issued on Jan. 7, 1997, to Nishikawa; U.S. Pat. No. 5,246,433, entitled "Elasticized Disposable Training Pant and Method of making the Same," which issued on Sep. 21, 1993, to Hasse; U.S. Pat. No. 5,464, 401, entitled "Elasticized Disposable Training Pant having Differential Extensibility," which issued on Sep. 21, 1993, to Hasse; U.S. Pat. No. 5,575,783, entitled "Absorbent Article with Dynamic Elastic Feature Comprising Elasticized Hip Panels," which issued on Nov. 19, 1996, to Clear; U.S. Pat. No. 5,779,691, entitled "Fastening Tape for a Sanitary Article Particularly Disposable Diaper," which issued on Jul. 14, 1998, to Schmitt; U.S. Pat. No. 5,143,679, entitled "Method for Sequentially Stretching Zero Strain Stretch Laminate Web to Impart Elasticity thereto Without Rupturing the Web," which issued on Sep. 1, 1992, to Weber; U.S. Pat. No. 4,834, 741 entitled "Diaper with Elastic Waist Band Elastic," which issued on May 30, 1989, to Sabee; and U.S. Pat. No. 4,968, 313, entitled "Diaper with Elastic Waist Band Elastic," which issued on Nov. 6, 1989, to Sabee.

Another process for mechanically deforming a web which can produce the deformed regions and corresponding heat induced by strain of the present invention is a process commonly referred to as a "SELF" or "SELF'ing", where SELF stands for Structural Elastic Like Film. While the process was originally developed for deforming polymer film to have beneficial structural characteristics, it has been found that the SELF'ing process can be used to produce beneficial structures in nonwoven webs. Processes, apparatus, and patterns produced via SELF are illustrated and described in U.S. Pat. No. 5,518,801 entitled "Sheet Materials Exhibiting Elastic-Like Behavior," which issued on May 21, 1996, to Charles W. Chappell et al. Other patents issued to Chappell include U.S. Pat. No. 5,691,035 entitled "Web Materials Exhibiting Elastic-like Behavior," issued Nov. 25, 1997; U.S. Pat. No. 5,723, 087 entitled "Web Materials Exhibiting Elastic-like Behavior," issued Mar. 3, 1998; U.S. Pat. No. 5,891,544 entitled "Web Materials Exhibiting Elastic-like Behavior" issued Apr. 6, 1999; U.S. Pat. No. 5,916,663 entitled "Web Materials Exhibiting Elastic-like Behavior," issued Jun. 29, 1999; and U.S. Pat. No. 6,027,483 entitled "Web Materials Exhibiting Elastic-like Behavior" issued Feb. 22, 2000.

Another process for mechanically deforming a web which can produce deformed regions and corresponding heat induced by strain of the present invention is a process that can best be described as "micro-SELF". Micro-SELF is a process that is similar in apparatus and method to that of the SELF process described above. The main difference between SELF and micro-SELF is the size and dimensions of the teeth on the toothed deformation member. The micro-SELF deformation member can be one of the deformation members forming the deformation zone in a preferred configuration having one patterned deformation member, e.g., micro-SELF deformation member, and one non-patterned grooved deformation member. However, in certain embodiments it may be preferable to use two micro-SELF deformation members having either the same or differing patterns, in the same or different corresponding regions of the respective deformation members. Such an apparatus can produce webs with deformed regions that, in nonwoven webs, can be described as tufts protruding from one or both sides of the processed web. The tufts can be closely spaced, but at least at their base can be spaced apart sufficiently to define void regions between tufts.

A process using micro-SELF to form tufts in a web substrate is disclosed in co-pending, commonly owned patent applications US 2006/0286343A1, filed Jun. 17, 2005. The tufts can be bonded at the tips using the process disclosed in U.S. Pat. No. 7,682,686. For tufts with bonded tips, color change can be limited to the tips only or extend to both the tips and sides of the loops, possibly in different shades, since additional heat is added to the tips of the tufts during bonding.

Another process for mechanically deforming a web which can produce deformed regions and corresponding second activated color regions according to the present invention is a process that can best be described as "rotary knife aperturing" (RKA). In RKA, a process and apparatus using intermeshing deformation members similar to that described above with respect to SELF or micro-SELF deformation members is utilized. The RKA process differs from SELF or micro-SELF in that the relatively flat, elongated teeth of a SELF or micro-SELF deformation member have been modified to be generally pointed at the distal end. Teeth, which are preferably heated, can be sharpened to cut through as well as deform a web to produce a three-dimensionally apertured web. In other respects such as tooth height, tooth spacing, pitch, depth of engagement, and other processing parameters, RKA and the RKA apparatus can be the same as described above with respect to SELF or micro-SELF. RKA teeth can have other shapes and profiles and the RKA process can be used to aperture fibrous webs, as disclosed in co-pending, commonly owned patent applications US 2005/0064136A1, filed Aug. 6, 2004, US 2006/0087053A1, filed Oct. 13, 2005, and US 2005/021753 filed Jun. 21, 2005.

Another process for mechanically deforming a web which can produce deformed regions comprising apertures according to the present invention is a process which uses a pin roll and a counter roll that rotate in opposite directions to form a nip through which the web substrate is fed as disclosed in U.S. Pat. No. 6,849,319. Pins protrude from the surface of the pin roll and holes are recessed into the counter roll. The pin roll and the counter roll are aligned so that pins of the pin roll mate with the holes of the counter roll. The pins may be heated. The method utilizing the pin roll and counter roll can be used to form apertured webs.

Another process for mechanically deforming a web substrate according to the present invention is embossing. Embossing of webs can provide improvements to the web such as increased bulk. During a typical embossing process, a web is fed through a nip formed between juxtaposed generally axially parallel rolls. Embossing elements on the rolls compress and/or deform the web. The embossed regions of the plies may produce an aesthetic pattern and provide a means for joining and maintaining the plies in face-to-face contacting relationship.

Embossing is typically performed by one of two processes; knob-to-knob embossing or nested embossing. Knob-to-knob embossing typically consists of generally axially parallel rolls juxtaposed to form a nip between the embossing elements on opposing rolls. Nested embossing typically consists of embossing elements of one roll meshed between the embossing elements of the other roll. Examples of knob-to-knob embossing and nested embossing are illustrated in the prior art by U.S. Pat. No. 3,414,459 issued Dec. 3, 1968 to Wells; U.S. Pat. No. 3,547,723 issued Dec. 15, 1970 to Gresham; U.S. Pat. No. 3,556,907 issued Jan. 19, 1971 to Nystrand; U.S. Pat. No. 3,708,366 issued Jan. 2, 1973 to Donnelly; U.S. Pat. No. 3,738,905 issued Jun. 12, 1973 to Thomas; U.S. Pat. No. 3,867,225 issued Feb. 18, 1975 to Nystrand; U.S. Pat. No. 4,483,728 issued Nov. 20, 1984 to Bauernfeind; U.S. Pat. No. 5,468,323 issued Nov. 21, 1995 to McNeil; U.S. Pat. No. 6,086,715 issued Jun. 11, 2000 to McNeil; U.S. Pat. No. 6,277,466 Aug. 21, 2001; U.S. Pat. No. 6,395,133 issued May 28, 2002 and U.S. Pat. No. 6,846,172 B2 issued to Vaughn et al. on Jan. 25, 2005.

Another process for mechanically deforming a web substrate according to the present invention is a method for selectively aperturing a nonwoven web which is disclosed in U.S. Pat. No. 5,658,639, U.S. Pat. No. 5,628,097, and U.S. Pat. No. 5,916,661. In this process a nonwoven web is weakened along a plurality of locations and then a tensioning force is applied causing the nonwoven web to rupture at the plurality of weakened locations creating a plurality of apertures in the nonwoven web coincident with the weakened locations. The web is weakened at a plurality of locations by passing it through a nip formed between a patterned calendar roll and an anvil roll. The patterned calendar roll has a plurality of protuberances that are disposed to precipitate a weakened, melt stabilized location in the web to affect a predetermined pattern of weakened, melt-stabilized locations in the nonwoven web. The tensioning force is subsequently applied to the web by passing it through an incremental stretching system comprising incremental stretching rollers referred to as ring rolls. The ring rolls, as described above under mechanical deformation processes, include a plurality of intermeshing teeth and grooves. Selectively apertured nonwoven webs including activatable colorant according to the present invention can include activated color regions in the weakened melt stabilized locations and the regions circumscribing the apertures as well as other areas of the web that are deformed as a result of the incremental stretching.

Each of the aforementioned deformation processes produce deformed regions comprising deformed elements (ridges and grooves, rib-like elements, apertures, tufts, embossments, etc.). The deformed regions can be produced uniformly throughout the web substrate or in individual zones. Depending on the equipment used, the size of each individual deformed element forming a deformed region can vary. For instance, each deformed element can have a length (or diameter) of less than 1.0 inch (2.54 cm), less than 0.5 inch (1.27 cm), less than 0.25 inch (0.635 cm) and less than 0.125 inch (0.318 cm). The number of deformed elements producing a deformed region and the size of the deformed region can also vary. For instance, the deformed regions can vary from an individual deformed element such as a single tuft, embossment, rib-like element or aperture to a plurality of deformed elements forming a deformed region where the size of the deformed region can range from 0.155 $in^2$ (1 $cm^2$) to 1550 $in^2$ (10,000 $cm^2$).

The substrates having activatable colorants according to the present invention are applicable, but not limited to absorbent articles such as diapers, sanitary napkins, tampons, tampon applicators, panty liners, incontinence devices, wipes and the like. For absorbent articles, the web substrates having activatable colorants can include topsheets, secondary topsheets, acquisition layers, absorbent cores and backsheets. Alternatively, the web substrates can be applicable to various components of the absorbent article such as fasteners, barrier cuffs, and landing zones. In addition to absorbent articles, web substrates having activatable colorants according to the present invention are applicable to trash bags, packaging films and dryer sheets.

Analytical Methodology—Hunter Color

The color scale values, utilized herein to define the darkness/lightness of the materials of the absorbent articles according to the present invention, is the widely accepted CIE LAB scale. Measurements are made with a Hunter Color reflectance meter. A complete technical description of the system can be found in an article by R. S. Hunter, 'photoelectric color difference Meter', Journal of the Optical Society of America, Vol. 48, pp. 985-95, 1958. Devices specially designed for the measurement of color on the Hunter scales are described in U.S. Pat. No. 3,003,388 to Hunter et al., issued Oct. 10, 1961. In general, Hunter Color "L" scale values are units of light reflectance measurement, and the higher the value is, the lighter the color is since a lighter colored material reflects more light. In particular, in the Hunter Color system the "L" scale contains 100 equal units of division. Absolute black is at the bottom of the scale (L=0) and absolute white is at the top of the scale (L=100). Thus in measuring Hunter Color values of the materials used in the absorbent articles according to the present invention, the lower the "L" scale value, the darker the material. The absorbent articles herein, and hence the materials of which the absorbent articles are made of, might be of any color provided that the L Hunter value defined herein is met.

Colors can be measured according to an internationally recognized 3D solid diagram of colors where all colors that are perceived by the human eye are converted into a numerical code.

The CIE LAB system is similar to Hunter L, a, b and is based on three dimensions, specifically $L^*$, $a^*$, and $b^*$.

When a color is defined according to this system $L^*$ represents lightness (0=black, 100=white), $a^*$ and $b^*$ independently each represent a two color axis, $a^*$ representing the axis red/green (+a=red, −a=green), while $b^*$ represents the axis yellow/blue (+b=yellow, −b=blue).

A color may be identified by a unique $\Delta E$ value (i.e., different in color from some standard or reference), which is mathematically expressed by the equation:

$$\Delta E^* = [(L^*_X - L^*_Y)^2 + (a^*_X - a^*_Y)^2 + (b^*_X - b^*_Y)^2]^{1/2}$$

'X' represents the standard or reference sample which may either be a 'white' sample or a 'colored' sample, e.g., one colored shade may be compared to another colored shade.

It is to be understood that the tristimulus color values and $\Delta E^*$ considered herein are those measured on the materials of interest (e.g., the colored and non-colored portions on the viewing surface of the topsheet disclosed herein).

The Hunter color meter quantitatively determines the amount (percent) of incident light reflected from a sample onto a detector. The instrument is also capable of analyzing the spectral content of the reflected light (e.g., how much green is in the samples). The Hunter color meter is configured to yield 3 values ($L^*$, $a^*$, $b^*$ and $\Delta E^*$ which is total color). The $L^*$ value is simply the percent of the incident (source) light that is reflected off a target sample and onto the detector. A shiny white sample will yield an $L^*$ value near 100 while a dull black sample will yield an $L^*$ value of about 0. The $a^*$ and $b^*$ value contains spectral information for the sample. Positive $a^*$ value indicates the amount of green in the sample.

Color Zone Measurement

The color of the first activated colored region and second activated colored region in a web substrate can be measured by the reflectance spectrophotometer according to the colors $L^*$, $a^*$, and $b^*$ values. The $L^*$, $a^*$, and $b^*$ values are measured from the surface of a substrate. The difference in color is calculated using the $L^*$, $a^*$, and $b^*$ values by the formula $\Delta E = [(L^*X - L^*Y)2 + (a^*X - a^*Y)2 + (b^*X - b^*Y)2]1/2$.

Herein, the 'X' in the equation may represent the first activated colored region or the second activated colored region and 'Y' may represent the color of another region against which the color of such region is compared. X and Y should not be the same two points of measurement at the same time. In other words, for any particular comparison of the difference in color, the location of X does not equal (≠) the location of Y.

Where greater than two shades of a color(s) are used, the 'X' and 'Y' values alternately include points of measurement in them also. The key to the $\Delta E$ calculation herein is that the 'X' and 'Y' values should not stem from the same measured point on the viewing surface. In those instances where there is effectively no non-colored portion within the confines of the measurement area, the 'X' values should flow from a point different in spatial relationship to the 'Y' values.

For the invention herein, values of $L^*$, $a^*$, and $b^*$ are measured using a standard, industry-recognized procedure. The substrate color is measured using a reflectance spectrophotometer in accordance with method ASTM E 1164-09a, "Standard Practice for Obtaining Spectrometric Data for Object-Color Evaluation". This standard method is followed but specific instrument settings and sampling procedure are given here for clarity.

Apparatus

Reflectance Spectrophotometer . . . 45°/0° Hunter Labscan XE, or equivalent HunterLab Headquarters, 11491 Sunset Hills Road, Reston Va. 20190-5280 Tel: 703-471-6870 Fax: 703-471-4237 http://www.hunterlab.com.

Standard plate . . . Standard Hunter White Tile Source: Hunter Color.

Equipment Preparation

1. Assure that the Spectrophotometer is configured as follows:

Illumination . . . Type D65

Standard Observer . . . 10°

Geometry . . . 45/0° Measurement angle

Port Diameter . . . 0.70 inch

Viewing area . . . 0.50 inch (and no smaller)

UV Filter: Nominal

2. Calibrate the spectrophotometer using standard black and white tiles supplied with the instrument according to manufacturer's instructions before beginning any testing.

Test Procedure

1. Operate the Hunter Colorimeter according to the instrument manufacturer's instructions.
2. Web samples should be measured laying flat over the 0.70 inch aperture on the instrument. A white tile should be placed behind the substrate.
3. Measure the same zones selected above for at least 3 replicate samples.

Calculation Reporting

1. Ensure that the reported results are really CIE $L^*$, $a^*$, $b^*$.
2. Record the $L^*$, $a^*$, $b^*$ values to the nearest 0.1 units.
3. Take the average $L^*$, $a^*$, $b^*$ for each zone measured.
4. Calculate $\Delta E^*$ between different shaded portions and $\Delta E^*$ between each shaded portion and the non-colored portion where the non-colored portion exists.

Human Sensitivity to Light

The human sensitivity threshold for the lightness of a dark green color is a $\Delta E^*$ of about 1.0. For a dark green color, if only the $a^*$ and $b^*$ change, human sensitivity is a $\Delta E^*$ of 2.4. In the context of an absorbent article (e.g., a sanitary napkin) it is highly likely that many people would not see a color difference if the $\Delta E^*$ is less than 2. This sensitivity is described in the following reference: "The Measurement of Appearance", by Hunter and Harold, 2nd edition, 1987, (ISBN 0-471-83006-2).

Chapter 4 of Hunter's book describes human color sensing and chapter 9 is about color scales. By making side-by side comparison, humans can differentiate up to 5 to 10 million different colors. In the 1940s, a researcher named MacAdam did human chromaticity discrimination experiments. He found the thresholds of sensitivity and showed these depend on the color. Later work by Brown and MacAdam came up with a logarithmic lightness dimension scale for human sensitivity to go with the earlier color scale. Based on the reduction to practice of the invention, experimentation and the foregoing work by Brown and MacAdam, it has been found herein that a $\Delta E \geq 3.5$ is the preferred range to effect proper differentiation between the shades that provides the proper appearance of depth. However, where the $\Delta E$ is as small as about 1 and still operates to provide a perception of depth between the shades, this $\Delta E$ is also contemplated and included herein.

Alternate Method of Color Measurement (for Small/Discrete Color Regions):

Each sample was laid flat and face down upon a Hewlett-Packard ScanJet 6300C scanner. The scanner lid was closed completely upon each sample and the sample was scanned. The resulting scanned sample images were saved under the "True Color" setting. Standards were measured the same way using the white and green Hunter tile numbers LX16566. The sample images were analyzed using Image J imaging and analysis software, ten locations within each distinct color region were sampled at random for each sample. Colors were measured in RGB color space. The RGB values were then mathematically transformed to XYZ and then to cieL*a*b* color space using the following algorithms:

Convert RGB to XYZ (Observer=2°, Illuminant=D65)

Reference: "A Standard Default Color Space for the Internet—sRGB" Michael Stokes (Hewlett-Packard), Matthew Anderson (Microsoft), Srinivasan Chandrasekar (Microsoft), Ricardo Motta (Hewlett-Packard) Version 1.10, Nov. 5, 1996 http://www.w3.org/Graphics/Color/sRGB 1. Convert from 8-Bit RGB:

Image J measures RGB in 8-bit. This step converts 8-bit to 0-1 scale for sRGB.

$$var\_R=(R/255)//R \text{ from 0 to 255}$$

$$var\_G=(G/255)//G \text{ from 0 to 255}$$

$$var\_B=(B/255)//B \text{ from 0 to 255}$$

2. Linearize RGB Values to Arrive at Standard RGB (sRGB):

RGB is a non-linear measurement. In order to linearize the expression in XYZ color-coordinate space this equation is employed.

if $(var\_R>0.04045)var\_R=((var\_R+0.055)/1.055)^{2.4}$ else $var\_R=var\_R/12.92$ if $(var\_G>0.04045)var\_G=((var\_G+0.055)/1.055)^{2.4}$ else $var\_G=var\_G/12.92$ if $(var\_B>0.04045)var\_B=((var\_B+0.055)/1.055)^{2.4}$ else $var\_B=var\_B/12.92$ 3. Convert to 0-100 XYZ Scale: XYZ is in a 0-100 Scale. This Converts to that Scale.

$$var\_R=var\_R*100$$

$$var\_G=var\_G*100$$

$$var\_B=var\_B*100$$

4. Derived Relationship for sRGB to XYZ Tri Stimulus Values:

This is the multiplication array that describes the relationship between sRGB and XYZ when an object is illuminated with D65.

//Observer.=2°, Illuminant=D65

$$X=var\_R*0.4124+var\_G*0.3576+var\_B*0.1805$$

$$Y=var\_R*0.2126+var\_G*0.7152+var\_B*0.0722$$

$$Z=var\_R*0.0193+var\_G*0.1192+var\_B*0.9505$$

XYZ to cieL*a*b*(Observer=2°, Illuminant=D65)

Reference: ISO Standard 13655 International Organization for Standardization, ISO Geneva. "ISO 13655:1996 Graphic Technology-Spectral Measurement and Colorimetric Computation for Graphic Arts Images" (1996).

1. Defines Slope in XYZ Color Coordinate Space $$var\_X=X/ref\_X//ref\_X=95.047$$

$$var\_Y=Y/ref\_Y//ref\_Y=100.000$$

$$var\_Z=Z/ref\_Z//ref\_Z=108.883$$

2. Current ISO Standard for Converting Between XYZ and L*a*b* if $(var\_X>0.08856)var\_X=var\_X^{(1/3)}$ else $var\_X=(7.787*var\_X)+(16/116)$ if $(var\_Y>0.08856)var\_Y=var\_Y^{(1/3)}$ else $var\_Y=(7.787*var\_Y)+(16/116)$ if $(var\_Z>0.08856)var\_Z=var\_Z^{(1/3)}$ else $var\_Z=(7.787*var\_Z)+(16/116)$ $$CIE\text{-}L*=(116*var\_Y)-16$$

$$CIE\text{-}a*=500*(var\_X-var\_Y)$$

$$CIE\text{-}b*=200*(var\_Y-var\_Z)$$

For each sample image, the delta L*, delta a*, and delta b* were calculated between the two distinct color regions using the following formula:

$$\text{Delta } L*=L*\text{color 1}-L*\text{color 2}$$

$$\text{Delta } a*=a*\text{color 1}-a*\text{color 2}$$

$$\text{Delta } b*=b*\text{color 1}-b*\text{color 2}$$

Total color differences (delta E*) between the two distinct color regions for each sample were then calculated using the following formula:

$$\text{Delta } E*=[(\text{Delta } L*)^2+(\text{Delta } a*)^2+(\text{Delta } b*)^2]^{1/2}$$

EXAMPLES

The following non-limiting examples are intended to illustrate potential embodiments of the present invention.

Example 1

Impact of Pre-Heating Step on Color After UV Activation

A spunbond nonwoven fabric was prepared comprising polypropylene and 1 weight percent Datalase Colour Change Pigment LT (from Datalase Ltd., Widnes, UK). Basis weight of the nonwoven is 28 grams per square meter. As made, the nonwoven is white.

Handsheets of this material were exposed to ultraviolet light in a Chromato-Vue C-75 UV darkroom cabinet set to 254 nm with an exposure time of 1 minute. The fabric turned a pale blue color. A second set of handsheets were passed through a laminator set to a temperature of 255° F. to uniformly heat the material. The handsheets were subsequently exposed to ultraviolet light under the same conditions as described above. The fabrics turned a darker shade of blue than the first set of materials. Color measurements, $\Delta C$ and $\Delta E$ values are provided in Table 1. The sample that had been pre-heated prior to UV activation has a significantly darker shade than the sample that underwent UV activation only.

TABLE 1

|         | L*   | A*   | B*    | $\Delta C$ | $\Delta E$ |
|---------|------|------|-------|------|------|
| As Made | 92.3 | −1.1 | 1.3   |      |      |
| UV Only | 88.3 | −1.8 | −2.1  | 1.1  | 5.3  |
| Heat + UV | 77.6 | −2.4 | −11.0 | 9.6  | 19.2 |

Example 2

Patterned Preheating Via Heated Nip and Masking

Figure 11:
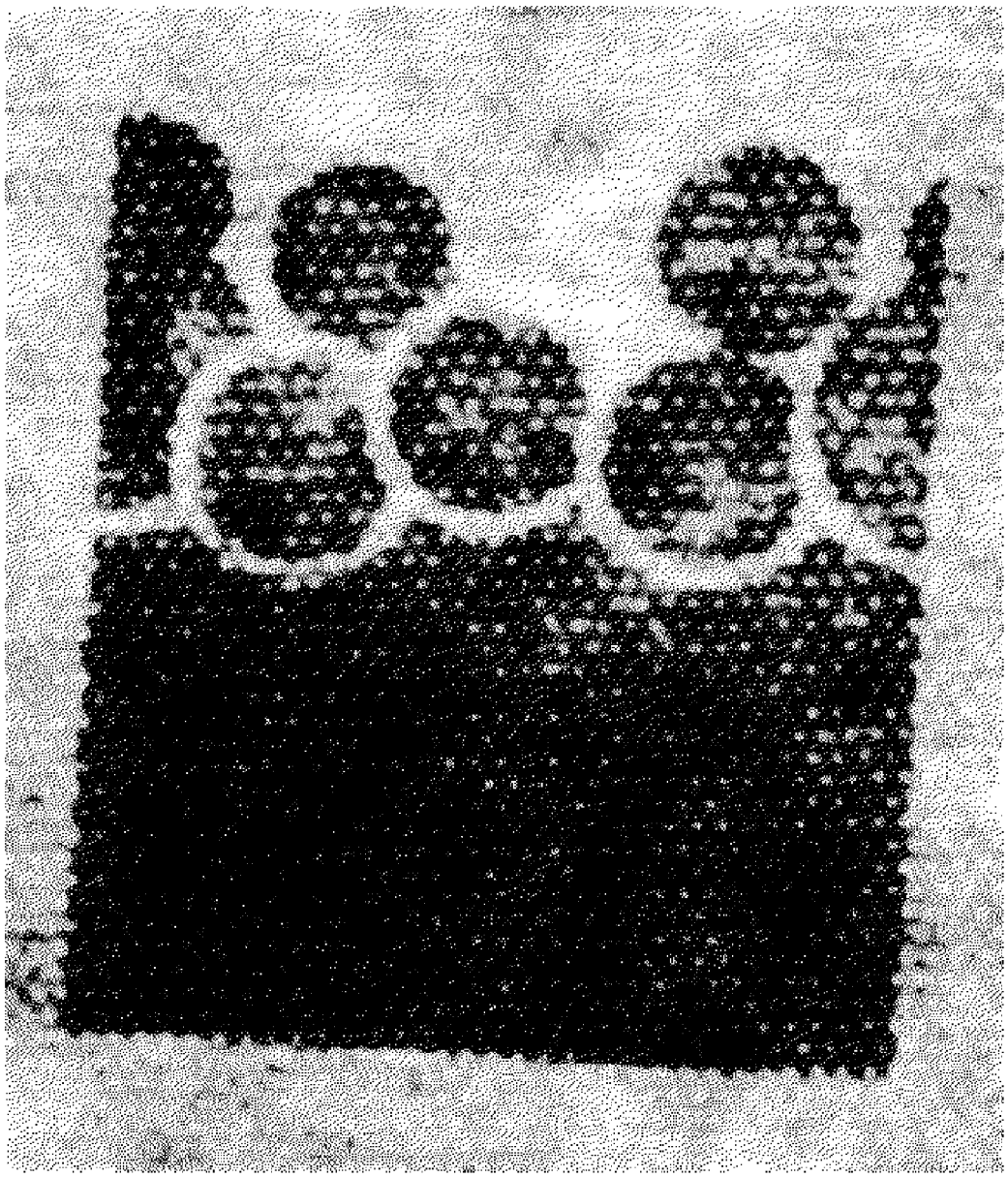
FIG. 11 is a plan black and white view of a nonwoven web substrate including an activatable colorant according to the present invention where the web substrate was masked with a pattern of joining circles prior to heating the web substrate such that the masked portions were not exposed to heating and the web substrate was subsequently exposed to ultraviolet light producing a pattern of dark shaded circles circumscribed by light shaded circles.

The same nonwoven as described in Example 1 was masked with a pattern of joining circles laser cut into a piece of paper. The nonwoven and paper were run together through a heated nip (laminator) at 124° C., masking some of the nonwoven from the heat of the nip roll. The paper mask was removed and the nonwoven then exposed to ultraviolet light in a Chromato-Vue C-74 darkroom cabinet set to 254 nm for 30 seconds. The entire nonwoven turned blue, but the shade of blue was darker in regions that were previously exposed to heat and lighter in regions that were masked from the heat. A black and white photograph of the resulting sample is provided in FIG. 11.

Example 3

Preheating Via Ultrasonic Bonding

Figure 12:
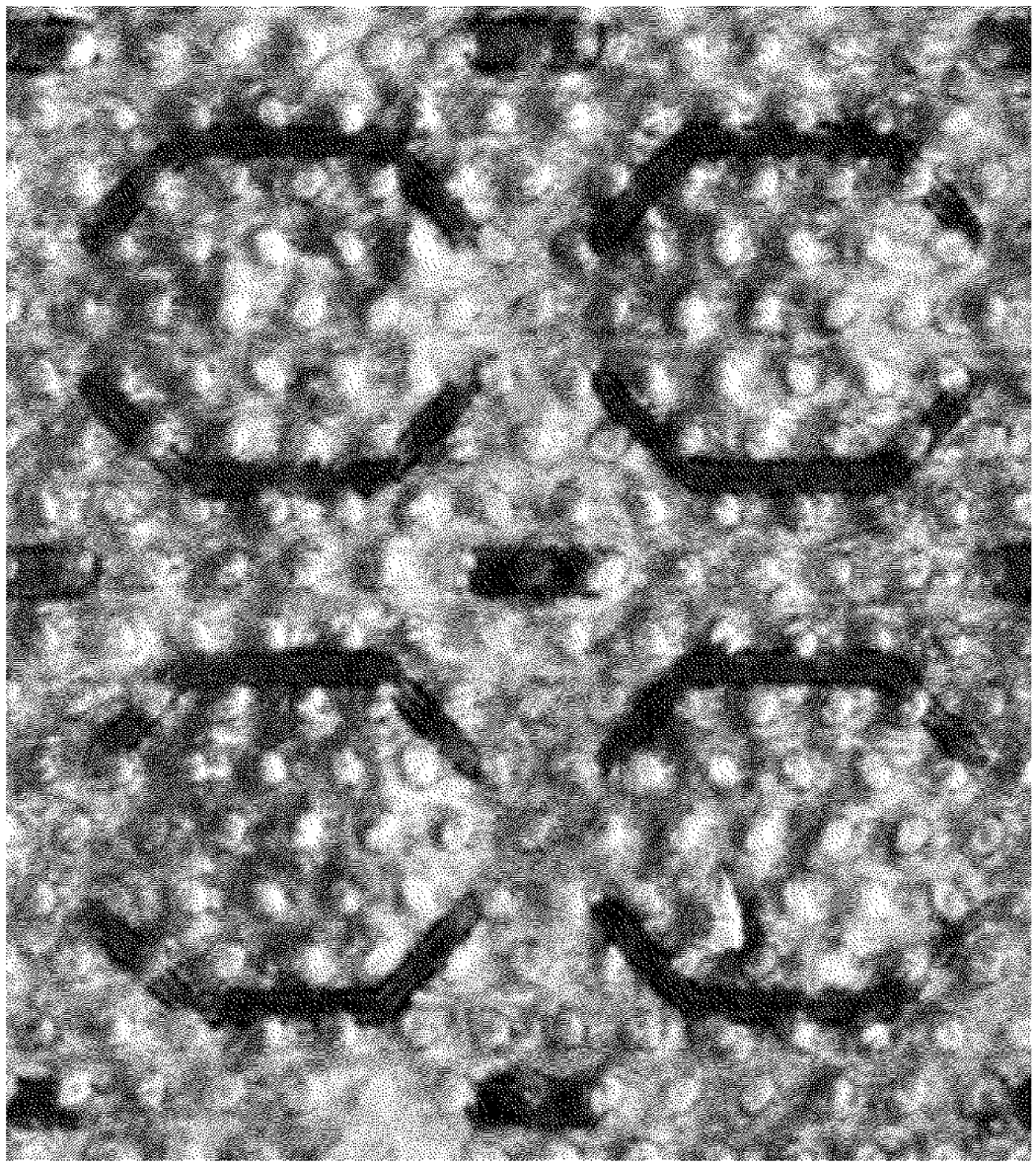
FIG. 12 is a plan black and white view of a nonwoven web substrate including an activatable colorant according to the present invention, where the web substrate was ultrasonically bonded to add a bonding pattern and subsequently exposed to ultraviolet light such that the entire nonwoven turned blue, however the bonded regions turned a darker shade of blue.

The same nonwoven as described in Example 1 was ultrasonically bonded to add a secondary bonding pattern using a Branson 900 model scan bonder and an acid etched bonding plate. After the bonding process, the material was still uniformly white in color. The material was then exposed to ultraviolet light in a Chromato-Vue C-74 darkroom cabinet set to 254 nm for 30 seconds. The entire nonwoven turned blue, however the secondary bond sites were a darker shade of blue than the surrounding nonwoven. A black and white photograph of the sample is provided in FIG. 12

Example 4

Preheating Via Heated Aperturing Process

The same nonwoven as described in Example 1 was apertured by hand-cranking the sample through a rotary knife aperturing process (0.060 inch pitch tooling at 93° C.). After aperturing, the material was still uniformly white in color. The material was then exposed to ultraviolet light in a Chromato-Vue C-74 darkroom cabinet set to 254 nm for 30 seconds. The entire nonwoven turned blue, however the area immediately surrounding the apertures turned a darker shade of blue than the base nonwoven, highlighting the presence of the aperture and providing a greater perception of depth.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or patent application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of producing color change in a substrate, the method comprising the steps of:
   a. providing a substrate comprising an activatable colorant;
   b. heating a region of the substrate forming a heated region; and
   c. applying electromagnetic radiation to the substrate to activate the activatable colorant producing a first activated color region in the heated region and a second activated color region separate from the heated region;
   wherein the step of heating a region of the substrate comprises mechanically deforming the region of the substrate wherein heat is induced by strain; and
   wherein the electromagnetic radiation comprises ultraviolet light.

2. The method according to claim 1 wherein the first activated color region is a first shade and the second activated color region is a second shade, and wherein the first shade and the second shade are the same color and the second shade is different from the first shade in lightness, darkness, and/or tone.

3. The method according to claim 2 wherein the first and second activated color regions are arranged to produce a perception of depth.

4. The method of claim 1 wherein the heated region of the substrate is heated to a temperature equal to or greater than the melting temperature of the activatable colorant.

5. The method of claim 1 wherein the heated region forms a pattern in the substrate.

6. The method according to claim 1 further comprising the step of masking a region of the substrate during the application of electromagnetic radiation wherein the activatable colorant is not activated in the masked region resulting in a non activated color region.

7. The method according to claim 1 wherein the substrate is selected from the group comprising films, nonwovens, air laids, laminates, fibers, filaments, particles, foams, and injection molded articles.

8. The method according to claim 1 wherein the substrate comprises a thermoplastic material.

9. The method according to claim 1 wherein the step of heating a region of the substrate comprises forming a plurality of apertures in the substrate producing a plurality of heated regions circumscribing the apertures.

10. The method according to claim 1 wherein the step of heating a region of the substrate comprises forming a plurality of thermal bond sites in the substrate producing a plurality of heated regions coinciding with the plurality of thermal bond sites.

11. The method according to claim 1 wherein the step of heating a region of the substrate comprises applying a heated topical additive to the substrate producing a topical additive region and a corresponding heated region coinciding with the topical additive region.

12. The method according to claim 11 wherein the topical additive is selected from the group comprising lotions, hot melt adhesives, coatings, odor control material, and perfumes.

13. The method according to claim 1 further comprising the step of mechanically deforming the substrate to produce a plurality of deformed regions within at least one of the first activated color region or the second activated color region or both the first and second activated color regions, wherein a plurality of third activated color regions are produced during formation of the deformed regions, and wherein the plurality of third activated color regions coincide with the plurality of deformed regions.

14. The method according to claim 13 wherein the plurality of deformed regions comprise apertures and wherein the step of mechanically deforming the substrate comprises the steps of:
   a. providing a first activation member comprising plurality of ridges and grooves;
   b. providing a second activation member comprising a plurality of teeth tapered from a base and a tip, wherein the teeth are joined to the second activation member at the base, and wherein the bases of the teeth have cross-sectional length dimensions greater than the cross-sectional width dimensions;
   c. forming a deformation zone between the first activation member and the second activation member wherein the plurality of ridges and grooves of the first activation member engage the plurality of teeth of the second activation member; and
   d. conveying the substrate through the deformation zone wherein the substrate is mechanically deformed forming a plurality of deformed regions comprising apertures extending through the substrate wherein the plurality of third activated color regions circumscribe the apertures.

15. The method according to claim 13 wherein the substrate is planar in the x-y plane and the plurality of deformed regions protrude in a z direction out of the x-y plane.

16. The method according to claim 15 wherein the plurality of deformed regions comprise ridges and grooves and wherein the step of mechanically deforming the substrate comprises the steps of:
   a. providing a first activation member comprising a plurality of teeth and grooves;
   b. providing a second activation member comprising a plurality of teeth and grooves that complement the plurality of teeth and grooves of the first activation member;
   c. forming a deformation zone between the first activation member and the second activation member wherein the plurality of teeth and grooves of the first activation member engage the plurality of teeth and grooves of the second activation member; and
   d. conveying the web substrate through the deformation zone wherein the substrate is mechanically deformed forming a plurality of deformed regions comprising ridges and grooves and wherein the plurality of third activated color regions coincide with the ridges and grooves.

17. The method according to claim 15 wherein the substrate is a nonwoven and the plurality of deformed regions comprise tufts and the step of mechanically deforming the substrate comprises the steps of:
   a. providing a first activation member having a plurality of spaced apart toothed ridges separated by circumferentially-extending grooves;
   b. providing a second activation member comprising a plurality of ridges and corresponding grooves extending unbroken about the entire circumference thereof and being disposed in an intermeshing relationship to form a nip with the first activation member;
   c. intermeshing the first activation member with the second activation member; and
   d. passing the substrate through the nip between the intermeshing first and second activation members, wherein the substrate is mechanically deformed forming a plurality of deformed regions comprising tufts extending from the substrate as the spaced apart toothed ridges on the first member intermesh with grooves on the second member, wherein the plurality of third activated color regions coincide with the tufts.

18. The method according to claim 15 wherein the plurality of deformed regions form a strainable network in the substrate exhibiting elastic-like behavior in response to an applied elongation along at least one axis thereof and wherein the step of mechanically deforming the substrate comprises the steps of:
   a. providing a first activation member comprising a plurality of toothed regions spaced apart by a plurality of grooved regions, the toothed regions comprising a plurality of teeth;
   b. providing a second activation member comprising a plurality of teeth which mesh with the teeth on the first activation member;
   c. intermeshing the teeth of the first activation member with the teeth of the second activation member;
   d. passing the substrate through the nip between the intermeshing first and second activation members, wherein the substrate is mechanically deformed forming a plurality of deformed regions comprising a strainable network in the substrate wherein the plurality of third activated color regions coincide with the strainable network, the strainable network comprises a first mechanically deformed region formed as the web substrate passes between grooves of a first roll and teeth on a second roll, and a second mechanically deformed region formed as the web substrate passes between teeth of the first roll and teeth on the second roll, the first mechanically deformed region provides a first, elastic-like resistive force to the applied elongation and the second mechanically deformed region provides a second resistive force to further applied elongation.

* * * * *